(12) United States Patent
Kamei

(10) Patent No.: US 8,697,042 B2
(45) Date of Patent: Apr. 15, 2014

(54) ORGANOPOLYSILOXANE AND COSMETIC CONTAINING IT

(75) Inventor: Masanao Kamei, Annaka (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 13/397,332

(22) Filed: Feb. 15, 2012

(65) Prior Publication Data

US 2012/0252757 A1 Oct. 4, 2012

(30) Foreign Application Priority Data

Mar. 29, 2011 (JP) .................................. 2011-72254

(51) Int. Cl.

| C07F 7/08 | (2006.01) |
|---|---|
| A61K 8/04 | (2006.01) |
| A61K 8/06 | (2006.01) |
| A61K 8/19 | (2006.01) |
| A61K 8/25 | (2006.01) |
| A61K 8/33 | (2006.01) |
| A61K 8/37 | (2006.01) |

(52) U.S. Cl.
USPC ........ 424/70.12; 556/431; 556/450; 556/434; 556/444; 556/446

(58) Field of Classification Search
USPC ................ 424/70.12; 556/431, 434, 444, 446
See application file for complete search history.

(56) References Cited

U.S. PATENT DOCUMENTS

| 4,431,789 | A | 2/1984 | Okazaki et al. |
|---|---|---|---|
| 6,576,623 | B1 | 6/2003 | Nakanishi et al. |
| 7,771,709 | B2 | 8/2010 | Nakanishi et al. |
| 2002/0131947 | A1* | 9/2002 | Nakanishi .................. 424/70.12 |
| 2010/0004201 | A1 | 1/2010 | Matsuo et al. |

FOREIGN PATENT DOCUMENTS

| EP | 1 847 262 | A1 | 10/2007 |
|---|---|---|---|
| EP | 1847262 | * | 10/2007 |
| JP | B2-4-15762 | | 3/1992 |
| JP | B2-4-20407 | | 4/1992 |
| JP | B2-5-12979 | | 2/1993 |
| JP | B2-5-13126 | | 2/1993 |
| JP | B2-6-62385 | | 8/1994 |
| JP | A-2005-154736 | | 6/2005 |
| JP | B2-3724988 | | 12/2005 |
| JP | A-2006-218472 | | 8/2006 |
| JP | A-2007-008915 | | 1/2007 |
| JP | A-2007-126359 | | 5/2007 |
| JP | B2-3976226 | | 9/2007 |

OTHER PUBLICATIONS

Takahashi et al. (Yukagaku, vol. 24, Issue 5, pp. 306-310, Published 1975, translation appended).*
Lagaly et al. (Applied Clay Science, 14, published 1999, pp. 83-103).*
Imhof et al. (Journal of Colloid and Interface Science, 192, Published 1997, pp. 368-374).*
Jun. 22, 2012 Extended European Search Report issued in European Patent Application No. 12001466.7.
May 28, 2013 Office Action issued in Japanese Patent Application No. 2011-072254 (with partial translation).

* cited by examiner

*Primary Examiner* — Richard Schnizer
*Assistant Examiner* — Alma Pipic
(74) *Attorney, Agent, or Firm* — Oliff PLC

(57) ABSTRACT

The invention provides an organopolysiloxane shown by the following formula (1);

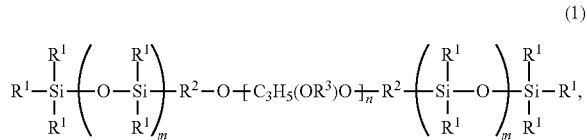

(1)

such that each $R^1$ independently represents a group selected from an alkyl group having 1 to 30 carbon atoms and optionally substituted with a fluorine atom, an aryl group having 6 to 30 carbon atoms, and an aralkyl group having 7 to 30 carbon atoms; each $R^2$ independently represents a divalent organic group having 2 to 15 carbon atoms and optionally intervened with an oxygen atom; and each $R^3$ independently represents a group selected from a polyoxyalkylene group shown by the following formula (2),

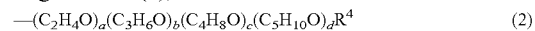

$$-(C_2H_4O)_a(C_3H_6O)_b(C_4H_8O)_c(C_5H_{10}O)_dR^4 \quad (2)$$

a hydrogen atom, and a group shown by the following formula (3),

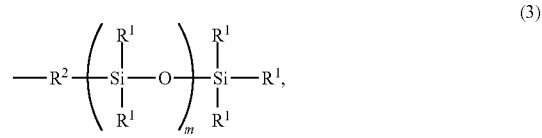

(3)

wherein at least one of $R^3$ in one molecule is the polyoxyalkylene group shown by the formula (2) with "m" representing an integer of 0 to 300 and "n" representing an integer of 1 to 10.

7 Claims, No Drawings

ORGANOPOLYSILOXANE AND COSMETIC CONTAINING IT

BACKGROUND OF THE INVENTION

1. Field of the Invention

The present invention relates to an organopolysiloxane and a cosmetic containing it.

2. Description of the Related Art

A silicone oil is used as an oil material in many applications because of its safety and so on. It is widely used in a cosmetic as well; especially a low-viscosity silicone oil having viscosity of 100 mm$^2$/second or less is widely used in applications such as, for example, skin care and make-up cosmetic and the like, because of its excellent spreading properties, refreshing feeling, and safety.

In the field of a cosmetic and the like, a silicone oil is generally used as emulsion; in that case, a silicone surfactant is used in many cases. As the silicone surfactant like this, such as for example, a polyether-modified silicone having a polyoxyalkylene group in the siloxane's terminal or side chain has been known (Japanese Examined Patent Publication No. H04-15762, Japanese Examined Patent Publication No. H04-20407, Japanese Examined Patent Publication No. H05-13126, Japanese Examined Patent Publication No. H06-62385, and Japanese Examined Patent Publication No. H05-12979). In addition, a polyether-modified silicone whose main chain siloxane moiety is branched (Japanese Patent No. 3724988) and a polyether-modified silicone of an ABA-type copolymer (silicone-hydrophilic group-silicone), as shown in the following formula, have been known (Japanese Patent Laid-Open Publication No. 2005-154736),

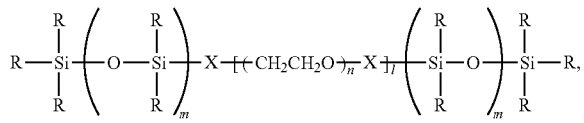

wherein X represents an arbitrary bonding group, such as a urethane group, a urea group, an amide group, an ester group, and an alkyl ether group. R represents a linear or a branched alkylene group having 1 to 12 carbon atoms, or a phenyl group, wherein "l" represents 1 to 5, "m" represents 40 to 90, and "n" represents 10 to 40.

As to the silicone surfactant, a silicone having, as other hydrophilic groups, a (poly)glycerin group (Japanese Examined Patent Publication No. S62-34039), a silicone having a branched siloxane moiety (Japanese Patent No. 3976226), and a (poly)glycerin-modified silicone as an ABA-type copolymer shown in the following formula (Japanese Patent Laid-Open Publication No. 2006-218472) have also been known. These silicones have been known also as a powder-dispersion stabilizer of a powder-containing cosmetic,

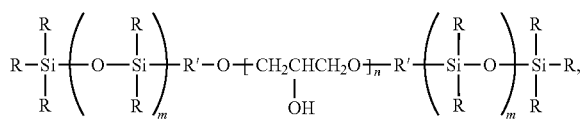

wherein R represents a linear or a branched alkyl group having 1 to 12 carbon atoms or a phenyl group, wherein R' is exemplified by an alkylene group having 2 to 11 carbon atoms. "m" represents 10 to 120 and "n" represents 1 to 11.

SUMMARY OF THE INVENTION

According to a different hydrophilic group, bonding position, hydrophilic-hydrophobic (silicone) balance, and so on, the above-mentioned silicone base surfactant is used depending on its use purpose; in particular, an ABA-type copolymer (a silicone-hydrophilic group-silicone) has excellent stability for the use in an emulsion cosmetic and a powder-containing cosmetic. However, in heretofore known silicone base surfactants, there have been problems in poor temporal stability and skin-contact property.

The present invention has been carried out to solve the above problem, and it is therefore an object of the present invention to provide an organopolysiloxane having excellent emulsion stability, and in addition, excellent powder-dispersion stability if powders are contained therein, excellent temporal stability, and excellent skin-contact property, and to provide a cosmetic containing this.

To solve the problems as mentioned above, the present invention provides an organopolysiloxane shown by the following formula (1),

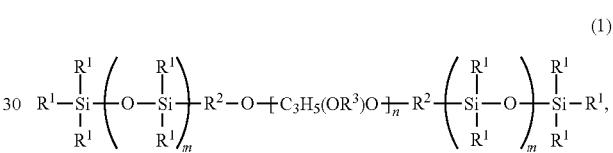

wherein each $R^1$ independently represents a group selected from an alkyl group having 1 to 30 carbon atoms and optionally substituted with a fluorine atom, an aryl group having 6 to 30 carbon atoms, and an aralkyl group having 7 to 30 carbon atoms; each $R^2$ independently represents a divalent organic group having 2 to 15 carbon atoms and optionally intervened with an oxygen atom; and each $R^3$ independently represents a group selected from a polyoxyalkylene group shown by the following formula (2), a hydrogen atom, and a group shown by the following formula (3), wherein at least one of $R^3$ in one molecular structure is the polyoxyalkylene group shown by the above formula (2) with "m" representing an integer of 0 to 300 and "n" representing an integer of 1 to 10, $$—(C_2H_4O)_a(C_3H_6O)_b(C_4H_8O)_c(C_5H_{10}O)_dR^4, \quad (2)$$

wherein $R^4$ represents a hydrogen atom or an alkyl group having 1 to 20 carbon atoms, and "a" to "d" represents an integer of 0 to 50 with satisfying $1 \le (a+b+c+d) \le 50$,

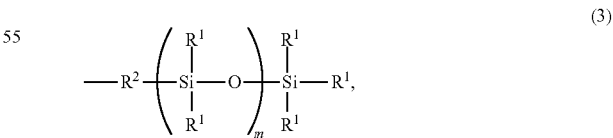

wherein $R^1$ and $R^2$ represent the same meanings as before; and "m" represents an integer of 0 to 300.

The organopolysiloxane having a novel structure of the polyoxyalkylene group like this is excellent in emulsion stability, and in addition, excellent in powder-dispersion stability if powders are contained therein, in temporal stability, and in skin-contact property.

Further, it is preferable that $R^2$ represent a divalent organic group shown by —$C_3H_6$— and $R^3$ represent a polyoxyalkylene group shown by the following formula (4),

—$(C_2H_4O)_a(C_3H_6O)_bR^4$, (4)

wherein "a" and "b" represent an integer of 0 to 50 with satisfying $1 \leq (a+b) \leq 50$. $R^4$ represents the same meaning as before.

When the organopolysiloxane has $R^2$ and $R^3$ as mentioned above, the organopolysiloxane improves further in emulsion stability, and in addition, in powder-dispersion stability if powders are contained therein, in temporal stability, and in skin-contact property.

Furthermore, It is also preferable that $R^2$ represent a divalent organic group shown by —$C_3H_6$— and each $R^3$ independently represent a polyoxyalkylene group shown by the following formula (4) and the group shown by the above formula (3), with "n" representing an integer of 2 to 10,

—$(C_2H_4O)_a(C_3H_6O)_bR^4$, (4)

wherein "a" and "b" represent an integer of 0 to 50 with satisfying $1 \leq (a+b) \leq 50$. $R^4$ represents the same meaning as before.

When the organopolysiloxane has $R^2$, $R^3$, and "n" as mentioned above, the organopolysiloxane improves further in emulsion stability, and in addition, in powder-dispersion stability if powders are contained therein, in temporal stability, and in skin-contact property.

Provided is a cosmetic wherein the organopolysiloxane mentioned above is contained therein with the amount thereof being 0.1 to 40% by mass relative to the total amount of the cosmetic.

The cosmetic as mentioned above is preferable because emulsion thereof can be made stably, powders may be stably dispersed if powders are contained therein, and in addition, the cosmetic is excellent in temporal stability, skin-contact property, and cosmetic durability.

Further, It is preferable that the cosmetic further contain water and is in the form of emulsion.

Even if the cosmetic contains water, emulsion thereof can be made stably, powders may be stably dispersed if powders are contained therein, and in addition, the cosmetic is excellent in temporal stability, skin-contact property, and cosmetic durability.

Furthermore, It is preferable that the cosmetic further contain any of a silicone oil, a glycol, an ester oil, a glyceride oil, and a mixture of them, and is in the form of non-aqueous emulsion.

Even if the cosmetic contains a silicone oil and so on, emulsion thereof can be made stably, powders may be stably dispersed if powders are contained therein, and in addition, the cosmetic is excellent in temporal stability, skin-contact property, and cosmetic durability.

Further, It is preferable that the cosmetic further contain a powder and is in the form of a liquid, a paste, or a solid, with the powder being dispersed therein.

If the organopolysiloxane mentioned above is blended in a powder-containing cosmetic, a cosmetic having highly dispersed powders may be obtained by powder-treatment effects (water resistance, cortical resistance, and dispersion stability into an oil material).

As explained above, the present invention can provide an organopolysiloxane having excellent emulsion stability, and in addition, excellent powder-dispersion stability if powders are contained therein, excellent temporal stability, and excellent skin-contact property; and a cosmetic containing this. Especially, if the organopolysiloxane mentioned above is blended in a powder-containing cosmetic, a cosmetic having highly dispersed powders may be obtained by powder-treatment effects (water resistance, cortical resistance, and dispersion stability into an oil material).

DETAILED DESCRIPTION OF THE PREFERRED EMBODIMENTS

Hereinafter, the organopolysiloxane of the present invention and the cosmetic containing this will be explained in more detail; but the present invention is not limited to them.

As mentioned above, in heretofore known silicon base surfactants, there have been problems in poor temporal stability and skin-contact property.

As a result of repeatedly conducting keen examination to achieve the problem, the present inventors have found out that the organopolysiloxane having a novel structure of the polyoxyalkylene group of the present invention was excellent in emulsion stability, and in addition, excellent in powder-dispersion stability if powders are contained therein, in temporal stability, and in skin-contact property; and as a result, the present invention could be accomplished.

[Organopolysiloxane]

Namely, the present invention provides an organopolysiloxane shown by the following formula (1);

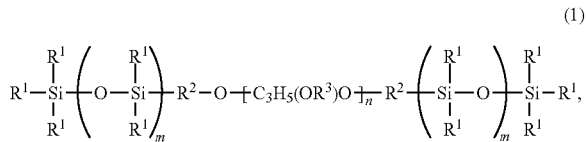

(1)

wherein each $R^1$ independently represents a group selected from an alkyl group having 1 to 30 carbon atoms and optionally substituted with a fluorine atom, an aryl group having 6 to 30 carbon atoms, and an aralkyl group having 7 to 30 carbon atoms; each $R^2$ independently represents a divalent organic group having 2 to 15 carbon atoms and optionally intervened with an oxygen atom; and each $R^3$ independently represents a group selected from a polyoxyalkylene group shown by the following formula (2), a hydrogen atom, and a group shown by the following formula (3), wherein at least one of $R^3$ in one molecule is the polyoxyalkylene group shown by the above formula (2) with "m" representing an integer of 0 to 300 and "n" representing an integer of 1 to 10,

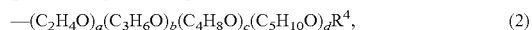
—$(C_2H_4O)_a(C_3H_6O)_b(C_4H_8O)_c(C_5H_{10}O)_dR^4$, (2)

wherein $R^4$ represents a hydrogen atom or an alkyl group having 1 to 20 carbon atoms, and "a" to "d" represents an integer of 0 to 50 with satisfying $1 \leq (a+b+c+d) \leq 50$,

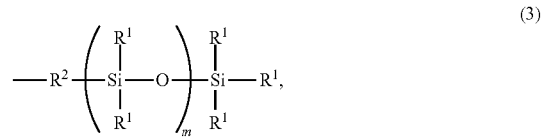

(3)

wherein $R^1$ and $R^2$ represent the same meanings as before; and "m" represents an integer of 0 to 300. Hereinafter, the present invention will be explained in detail.

In the formula (1), each $R^1$ independently represents a group selected from an alkyl group having 1 to 30 carbon atoms and optionally substituted with a fluorine atom, an aryl group having 6 to 30 carbon atoms, and an aralkyl group having 7 to 30 carbon atoms. In $R^1$, the alkyl group having 1 to 30 carbon atoms and optionally substituted with a fluorine atom is not particularly restricted; and illustrative example thereof includes an alkyl group such as a methyl group, an ethyl group, a propyl group, a butyl group, a pentyl group, a hexyl group, a heptyl group, an octyl group, a nonyl group, and a decyl group; a cyclic alkyl group such as a cyclopentyl group and a cyclohexyl group; and the foregoing groups substituted with a fluorine atom, especially a trifluoropropyl group, a heptadecafluorodecyl group, and so on. The aryl group having 6 to 30 carbon atoms is not particularly restricted; and illustrative example thereof includes a phenyl group and a tolyl group. The aralkyl group having 7 to 30 carbon atoms is not particularly restricted; and illustrative example thereof includes a benzyl group and a phenethyl group.

$R^1$ is preferably an alkyl group having 1 to 15 carbon atoms or a phenyl group, or more preferably, a methyl group and a butyl group. Further, it is preferable that 50% or more of $R^1$ contained in the organopolysiloxane molecule shown by the formula (1) is a methyl group, or more preferably 70% or more of $R^1$ is a methyl group.

In the formula (1), each $R^2$ independently represents a divalent organic group having 2 to 15 carbon atoms and optionally intervened with an oxygen atom. $R^2$ is not particularly restricted; and illustrative example of $R^2$ includes —$(CH_2)_2$—, —$(CH_2)_3$—, —$(CH_2)_4$—, —$CH_2CH(CH_3)CH_2$—, —$(CH_2)_8$—, —$(CH_2)_{11}$—, —$(CH_2)_3$—O—$(CH_2)_2$—, and —$(CH_2)_2$—O—$(CH_2)_3$—, while —$(CH_2)_2$—, —$(CH_2)_3$—, and —$CH_2CH(CH_3)CH_2$— are preferable.

In the formula (1), each $R^3$ independently represents a group selected from a polyoxyalkylene group shown by the following formula (2), a hydrogen atom, and a group shown by the following formula (3), wherein at least one of $R^3$ in one molecule is the polyoxyalkylene group shown by the formula (2),

  (2)

—$(C_2H_4O)_a(C_3H_6O)_b(C_4H_8O)_c(C_5H_{10}O)_dR^4$, wherein $R^4$ represents a hydrogen atom or an alkyl group having 1 to 20 carbon atoms, and "a" to "d" represents an integer of 0 to 50 with satisfying $1 \le (a+b+c+d) \le 50$,

  (3)

wherein $R^1$ and $R^2$ represent the same meanings as before; and "m" represents an integer of 0 to 300. The group shown by the formula (2) contains at least one repeating unit of ethylene oxide ($C_2H_4O$), propylene oxide ($C_3H_6O$), butylene oxide ($C_4H_8O$), and pentylene oxide ($C_5H_{10}O$), and may also be a group of a random or a block copolymer of them; preferably the group of ethylene oxide, propylene oxide, or ethylene oxide-propylene oxide copolymer.

In the formula (2), $R^4$ represents a hydrogen atom or an alkyl group having 1 to 20 carbon atoms, and "a" to "d" represents an integer of 0 to 50 with satisfying $1 \le (a+b+c+d) \le 50$. The alkyl group having 1 to 20 carbon atoms in $R^4$ is not particularly restricted; and illustrative example of $R^4$ includes a methyl group, an ethyl group, a butyl group, an octyl group, a lauryl group, and a stearyl group, while $R^4$ is preferably a hydrogen atom, a methyl group, and a butyl group.

Further, in the formula (2), "a" to "d" represents an integer of 0 to 50 with satisfying $1 \le (a+b+c+d) \le 50$. "d" is preferably 0, while the sum of "a" to "d" is preferably $1 \le (a+b+c+d) \le 30$, or more preferably $1 \le (a+b+c+d) \le 20$.

In the formula (3), $R^1$ and $R^2$ represent the same meanings as before; and "m" represents an integer of 0 to 300.

Further, in the formula (1), "m" represents an integer of 0 to 300 and "n" represents an integer of 1 to 10. "m" is preferably 0 to 150, or more preferably 2 to 100. "n" is preferably 1 to 6, or more preferably 2 to 5.

In the organopolysiloxane of the present invention as mentioned above, in particular, $R^2$ is preferably the divalent organic group shown by —$C_3H_6$—, and $R^3$ is preferably the polyoxyalkylene group shown by the following formula (4), —$(C_2H_4O)_a(C_3H_6O)_bR^4$,  (4)

wherein "a" and "b" represent an integer of 0 to 50 with satisfying $1 \le (a+b) \le 50$, and $R^4$ represents the same meaning as before. When the organopolysiloxane has $R^2$ and $R^3$ as mentioned above, the organopolysiloxane is more excellent in emulsion stability, and in addition, more excellent in powder-dispersion stability if powders are contained therein, in temporal stability, and in skin-contact property. The organopolysiloxane as mentioned above is shown by the following formula (5),

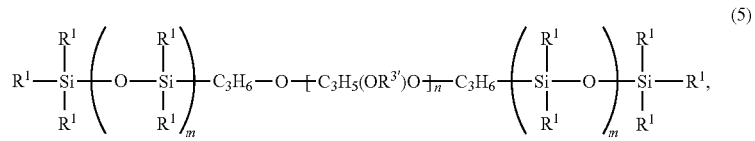  (5)

wherein $R^1$, "n", and "m" represent the same meanings as before; and $R^{3'}$ represents the polyoxyalkylene group shown by the formula (4).

Further, in the organopolysiloxane, it is preferable that $R^2$ be a divalent organic group shown by —$C_3H_6$—, each $R^3$ independently be the polyoxyalkylene group shown by the following formula (4) and the group shown by the formula (3), and "n" representing an integer of 2 to 10, —$(C_2H_4O)_a(C_3H_6O)_bR^4$,  (4)

wherein "a" and "b" represents an integer of 0 to 50 with satisfying $1 \le (a+b) \le 50$, and $R^4$ represents the same meaning as before. When the organopolysiloxane has $R^2$, $R^3$, and "n" as mentioned above, the organopolysiloxane is more excellent in emulsion stability, and in addition, more excellent in powder-dispersion stability if powders are contained therein, in temporal stability, and in skin-contact property. The organopolysiloxane as mentioned above is shown by the following formula (6),

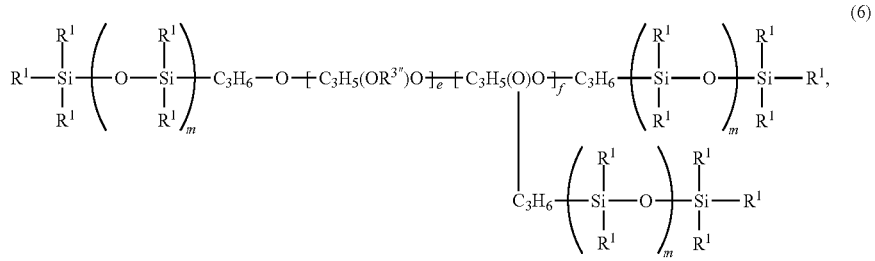

(6)

wherein $R^1$ and "m" represent the same meanings as before, and $R^{3''}$ represents the polyoxyalkylene group shown by the formula (4). "e" and "f" represent an integer of 1 to 9 with satisfying $2 \leq (e+f) \leq 10$.

[Synthesis Method of the Organopolysiloxane]

Synthesis method of the organopolysiloxane of the present invention is not particularly restricted; and the following synthesis method may be shown as an example of it.

(Step 1: Synthesis of a Polyglycerin Compound Containing an Alkenyl Group)

An epoxy compound, such as a monoalkenyl glycidyl ether and glycidol, and a compound containing a hydroxy group, such as glycerin and glycerin monoallyl ether, are subjected to a ring-opening reaction of the epoxy group thereof in the presence of a base catalyst to obtain a polyglycerin compound containing an alkenyl group. By changing mole ratio of the respective raw materials, a compound having different degree of polymerization can be synthesized.

(Step 2: Synthesis of a Compound Containing a Polyoxyalkylene Group)

By using the hydroxy group of the polyglycerin compound containing an alkenyl group obtained in Step 1 as an origination point, a ring opening reaction of an alkylene oxide is carried out in the presence of a base catalyst to obtain a compound containing a polyoxyalkylene group.

(Step 3: Synthesis of an Organopolysiloxane Containing a Polyoxyalkylene Group)

The compound obtained in Step 2 and a polysiloxane having hydrogen on its one end are subjected to an addition reaction between the alkenyl group and the Si—H group contained therein in the presence of a platinum or a rhodium catalyst to obtain an organopolysiloxane containing a polyoxyalkylene group.

The ring-opening reactions between the hydroxy group and the epoxy group in Step 1 and Step 2 are known to those skilled in the art; and thus, the base catalyst used therein is not particularly restricted, while KOH, NaOH, NaOCH$_3$, and so on may be used. Amount of the base catalyst to be used is 0.2 to 2% by mol, or preferably 0.2 to 1% by mol relative to 100% by mol of the compound having the hydroxy group.

During the reaction in Step 1, various kinds of isomers may be contained depending on the blending composition of the raw materials. For example, in the reaction between glycerin and 2 moles of allyl glycidyl ether, a mixture of isomers shown below is formed.

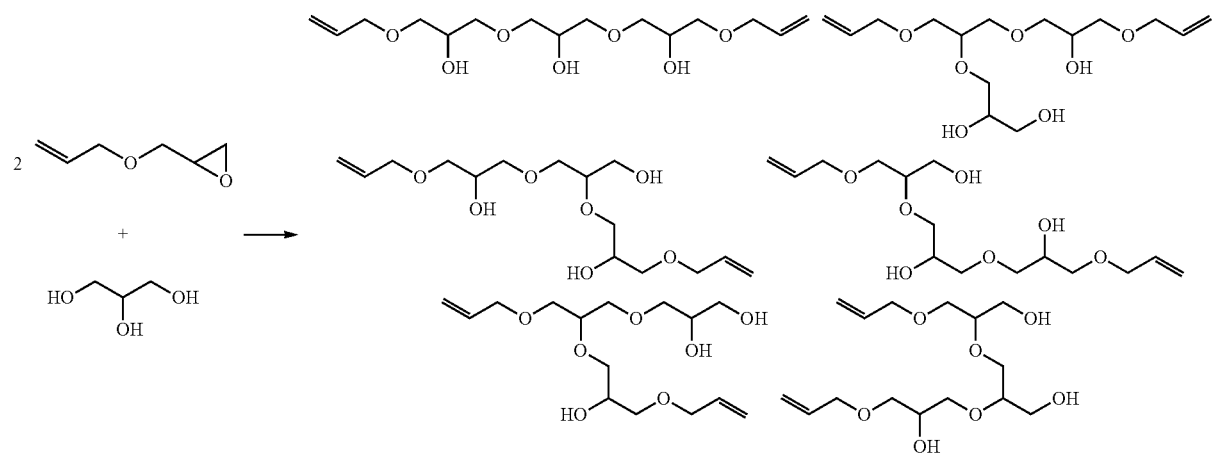

The addition reaction in Step 3 is preferably carried out in the presence of a platinum or a rhodium catalyst; for example, a chloroplatinic acid, an alcohol-modified chloroplatinic acid, a chloroplatinic acid-vinyl siloxane complex, and so on may be preferably used. Here, the catalyst amount to be used may be an effective amount; for example, the amount as platinum or rhodium is 50 ppm or less, or preferably 20 ppm or less.

The addition reaction in Step 3 may be carried out in an organic solvent as appropriate; illustrative example of the organic solvent includes an aromatic hydrocarbon such as toluene and xylene; a lower alcohol such as ethanol and isopropyl alcohol; an aliphatic or an alicyclic hydrocarbon such as n-pentane, n-hexane, and cyclohexane; a halogen-containing hydrocarbon such as dichloromethane, chloroform, and carbon tetrachloride; an ether such as tetrahydrofurane and dioxane; and a ketone such as acetone and methyl ethyl ketone. Preferably, a hydrocarbon solvent or a lower alcohol is used.

Conditions of the addition reaction are not particularly restricted; when a solvent is used, the reaction is carried out preferably under reflux of the solvent for 1 to 10 hours.

[Cosmetic]

The organopolysiloxane of the present invention synthesized as mentioned above is preferably used in a cosmetic for external use on skin and hair. The present invention provides a cosmetic wherein the organopolysiloxane mentioned above is contained therein with the amount thereof being 0.1 to 40% by mass relative to the total amount of the cosmetic. The cosmetic as mentioned above is preferable because the cosmetic is excellent in emulsion stability, and in addition, excellent in powder-dispersion stability if powders are contained therein, in temporal stability, in skin-contact property, and in cosmetic durability. Amount of the organopolysiloxane to be blended is 0.1 to 40% by mass, or preferably 0.5 to 20% by mass, relative to the total amount of the cosmetic.

In addition, it is preferable that the cosmetic of the present invention further contain water and is in the form of emulsion. Even if the cosmetic contains water as mentioned above, emulsion thereof can be made stably, powders may be stably dispersed if powders are contained therein, and in addition, the cosmetic is excellent in temporal stability, skin-contact property, and cosmetic durability; and thus, the cosmetic like this is preferable. Especially, the organopolysiloxane of the present invention may be contained as an emulsifying agent in the cosmetic that contains water as a polar solvent.

In addition, it is preferable that the cosmetic of the present invention contain any of a silicone oil, a glycol, an ester oil, a glyceride oil, and a mixture of them, and is in the form of non-aqueous emulsion. Even if the cosmetic contains a silicone oil and so on as mentioned above, emulsion thereof can be made stably, powders may be stably dispersed if powders are contained therein, and in addition, the cosmetic is excellent in temporal stability, skin-contact property, and cosmetic durability; and thus, the cosmetic like this is preferable. The organopolysiloxane of the present invention may be contained as an emulsifying agent used in a cosmetic that contains a polar solvent usually used, such as a silicone oil, a glycol, an ester oil, and a glyceride oil. The silicone oil, the glycol, the ester oil, the glyceride oil, and so on as mentioned above will be exemplified later.

In addition, it is preferable that the cosmetic of the present invention contain powders and is in the form of a liquid, a paste, or a solid, with the powders being dispersed therein. If the organopolysiloxane is blended in a powder-containing cosmetic as mentioned above, a cosmetic having highly dispersed powders may be obtained by powder-treatment effects (water resistance, cortical resistance, and dispersion stability into an oil material). The organopolysiloxane is especially suitable as a dispersing agent for a cosmetic that contains powders. Amount of the organopolysiloxane to be blended for a cosmetic that contains powders is 1 to 40 parts by mass, or preferably 1 to 20 parts by mass, relative to 100 parts by mass of the powders contained therein.

[Other Components]

The cosmetic of the present invention may contain other components without adversely affecting the object of the present invention. Illustrative example thereof will be shown below.

(Oil Material)

Into the cosmetic of the present invention can be blended one, or two or more, of an oil material depending on its purpose. An oil material in any form of a solid, a semi-solid, and a liquid can be used provided that it is used in a usually used cosmetic; illustrative example of the oil material includes a natural plant and animal fatty oil or a semi-synthetic fatty oil, a hydrocarbon oil, a higher fatty acid, a higher alcohol, an ester oil, a glyceride oil, a usually used silicone oil, and a fluorinated oil material.

Illustrative example of the natural plant and animal fatty oil and the semi-synthetic fatty oil includes an avocado oil, a linseed oil, an almond oil, an insects wax, a perilla oil, an olive oil, a cacao butter, a kapok wax, a kaya oil, a carnauba wax, a lever oil, a candellila wax, a purified candellila wax, a beef tallow, a newts-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tong oil, a cinnamon oil, a jojoba wax, squalane, squalene, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse fat, a persic oil, a palm oil, a palm kernel oil, a castor oil, a cured castor oil, a methyl ester of castor oil fatty acid, a sunflower oil, a grape seed oil, a bayberry wax, a jojoba oil, a macademia nut oil, a bees wax, a mink oil, a meadowfoam seed oil, a cotton seed oil, a cotton wax, a Japan wax, a Japan wax kernel oil, a montan wax, a coconut oil, a cured coconut oil, a tri-coconut fatty acid glyceride, a mutton tallow, a peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil. Meanwhile, POE means polyoxyethylene.

Illustrative example of the hydrocarbon oil includes a linear, a branched, and a volatile hydrocarbon oil; specifically such as an ozocerite, an α-olefin oligomer, a light isoparaffin, isododecane, isohexadecane, a light liquid isoparaffin, squalane, a synthetic squalane, a vegetable squalane, squalene, a ceresin, a paraffin, a paraffin wax, a polyethylene wax, a polyethylene/polypropylene wax, ethylene/propylene/styrene copolymer, butylene/propylene/styrene copolymer, a liquid paraffin, a liquid isoparaffin, a pristane, polyisobutylene, a hydrogenated isobutene, a microcrystalline wax, and vaseline. Illustrative example of the higher fatty acid includes lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Illustrative example of the higher alcohol includes lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol), and monooleyl glyceryl ether (selachyl alcohol).

Illustrative example of the ester oil includes diisobutyl adipate, 2-hexyldecyl adipate, 2-heptylundecyl adipate, an N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, isopropyl lauroylsarcosinate ester, and diisostearyl malate. Illustrative example of the glyceride oil includes acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

Illustrative example of the silicone oil includes a linear or a branched organopolysiloxane having low to high viscosity such as dimethyl polysiloxane, tristrimethylsiloxy methyl silane, caprylyl methicone, phenyl trimethicone, tetrakistrimethylsiloxy silane, methyl phenyl polysiloxane, methyl hexyl polysiloxane, methyl hydrogen polysiloxane, and dimethylsiloxane/methyl phenyl siloxane copolymer; a cyclic organopolysiloxane such as octamethyl cyclotetrasiloxane, decamethyl cyclopentasiloxane, dodecamethyl cyclohexasiloxane, tetramethyl tetrahydrogen cyclotetrasiloxane, and tetramethyl tetraphenyl cyclotetrasiloxane; a silicone rubber such as an amino-modified organopolysiloxane, a pyrrolidone-modified organopolysiloxane, a pyrrolidone carboxylate-modified organopolysiloxane, a dimethyl polysiloxane gum of a high degree of polymerization, an amino-modified organopolysiloxane gum, and a dimethylsiloxane/methyl phenyl siloxane copolymer gum; a solution of a silicone gum or rubber of a cyclic organopolysiloxane, trimethylsiloxy silicic acid, a cyclic siloxane solution of trimethylsiloxy silicic acid, a silicone modified with a higher alkoxy such as stearoxysilicone, a higher fatty acid-modified silicone, an alkyl-modified silicone, a long chain alkyl-modified silicone, an amino acid-modified silicone, a fluorine-modified silicone, and a solution containing a dissolved silicone resin.

Illustrative example of the fluorinated oil material includes perfluoro polyether, perfluoro decalin, and perfluoro octane. Amount of these oil materials to be blended is dependent on the form of the cosmetic; but it is preferably in the range of 1 to 98% by mass relative to the totality of the cosmetic.

(Water)

The cosmetic of the present invention may be blended with water depending on the purpose thereof. Amount of water to be blended is dependent on the form of the cosmetic; but it is preferably in the range of 1 to 95% by mass relative to the totality of the cosmetic.

(Alcohol)

The cosmetic of the present invention may use, depending on the purpose thereof, one, or two or more kinds of a lower alcohol having 2 to 5 carbon atoms and a polyvalent alcohol having 2 to 10 carbon atoms. Illustrative example of the alcohol includes a lower alcohol such as ethanol and isopropanol; a sugar alcohol such as sorbitol and maltose; a sterol such as cholesterol, sitosterol, phytosterol, and lanosterol; and a polyvalent alcohol such as butylene glycol, propylene glycol, dibutylene glycol, and pentylene glycol. Amount thereof to be blended is preferably in the range of 0.1 to 98% by mass relative to the totality of the cosmetic.

(Water-Soluble or Water-Swelling Polymer)

The cosmetic of the present invention may use, depending on the purpose thereof, a water-soluble or a water-swelling polymer. Especially preferable is one, or two or more water-soluble thickeners selected from a plant polymer, a microbial polymer, an animal polymer, a starch polymer, a cellulose polymer, an alginic acid polymer, a polyoxyethylene polyoxypropylene copolymer, an acryl polymer, and an inorganic water-soluble polymer. Illustrative example thereof includes a plant polymer such as an Arabia gum, tragacanth, galactan, a carob gum, a guar gum, a karaya gum, carrageenan, pectin, agar, quince seed (marmelo), starch (rice, corn, potato, wheat, and so on), an algae colloid, a trant gum, and a locust bean gum; a microbial polymer such as a xanthan gum, dextran, succinoglucan, and pullulan; an animal polymer such as collagen, casein, albumin, and gelatin; a starch polymer such as carboxymethyl starch and methylhydroxypropyl starch; a cellulose polymer such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose; an alginic acid polymer such as sodium alginate and propylene glycol alginate ester; a vinyl polymer such as polyvinyl methyl ether and carboxy vinyl polymer; a polyoxyethylene polymer; a polyoxyethylene polyoxypropylene copolymer; an acryl polymer such as sodium polyacrylate, polyethyl acrylate, polyacrylamide, and an acryloyldimethyl taurate salt copolymer; other synthetic water-soluble polymer such as polyethyleneimine and an cationic polymer; and an inorganic water-soluble polymer such as bentonite, aluminum magnesium silicate, montomorillonite, beidellite, nontronite, saponite, hectorite, and anhydrous silicic acid. Amount of these polymers to be blended is preferably in the range of 0.1 to 25% by mass relative to the totality of the cosmetic.

(Powder)

The cosmetic of the present invention may use, depending on the purpose thereof, one or two or more kinds of powders. As to the powder like this, any powder may be used regardless of its form (spherical, needle-like, plate-like, and so on), its particle diameter (fumed, microparticle, pigment-class, and so on), and its particle structure (porous, non-porous, and so on), provided that the powder is used in a usual cosmetic. Illustrative example of the powder includes an inorganic powder, an organic powder, a surfactant metal salt powder, a color pigment, a pearl pigment, a metal powder pigment, and a natural dye. Specific example of the inorganic powder includes titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, pink mica, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montomorillonite, hectorite, zeolite, ceramics powder, dibasic calcium phosphate, alumina, aluminum hydroxide, boron nitride, and silica. Specific example of the organic powder includes a polyamide powder, a polyester powder, a polyethylene powder, a polypropylene powder, a polystyrene powder, a polyurethane, a bezoguanamine powder, a polymethyl benzoguanamine powder, a tetrafluoroethylene powder, a polymethyl methacrylate powder, cellulose, a silk powder, a nylon powder, a 12 nylon, a 6 nylon, a silicone powder, styrene-acrylic acid copolymer, divinyl benzene-styrene copolymer, a vinyl resin, an urea resin, a phenolic resin, a fluorinated resin, a silicone resin, an acryl resin, a melamine resin, an epoxy resin, a polycarbonate resin, a fine crystalline fiber powder, a starch powder, and lauroyl lysine. Specific example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc. Specific example of the color pigment includes an inorganic red pigment such as iron oxide, iron hydroxide, and iron titanate; an inorganic brown pigment such as γ-iron oxide; an inorganic yellow pigment such as a yellow iron oxide and a yellow earth; an inorganic black pigment such as a black iron oxide and a carbon black; an inorganic purple pigment such as a manganese violet and a cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a synthetic resin powder obtained by hybridization of these powders. Specific example of the pearl pigment includes a mica coated with titanium oxide, oxychloro bismuth, oxychloro bismuth coated with titanium oxide, a talc coated with titanium oxide, a fish scale foil, and a color mica coated with titanium oxide. Specific example of the metal powder pigment includes an aluminum powder, a copper powder, and a stainless powder. Specific example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Specific example of the natural dye includes a powder selected from carminic acid, laccaic acid, carthamin, brazilin, and crocin.

In addition, usable are a powder obtained by hybridizing, or treating these powders, with a general oil material, a silicone oil, a fluorine-containing compound, a surfactant, and the like, without adversely affecting the effects of the present invention; a powder treated with a hydrolysable silyl group or with an alkyl group having a hydrogen atom directly bonded to a silicon atom; a linear type and/or a branched type organopolysiloxane having a hydrolysable silyl group or a hydrogen atom directly bonded to a silicon atom; a linear type and/or a branched type organopolysiloxane having a hydrolysable silyl group or a hydrogen atom directly bonded to a silicon atom and co-modified with a long chain alkyl group; a linear type and/or a branched type organopolysiloxane having a hydrolysable silyl group or a hydrogen atom directly bonded to a silicon atom and co-modified with a polyoxyalkylene group; an acryl-silicone copolymer having a hydrolysable silyl group or a hydrogen atom directly bonded to a silicon atom; and, as appropriate, a mixture of one, or two or more of them.

Amount of the powder to be blended is preferably 0.1 to 99% by mass relative to the totality of the cosmetic. Especially in the case of a powdery solid cosmetic, the amount thereof is preferably 80 to 99% by mass relative to the totality of the cosmetic.

(Surfactant)

The cosmetic of the present invention may also use, depending on the purpose thereof, one or two or more kinds of surfactants. As to the surfactants like this, there are an anionic, a cationic, a nonionic, and an amphoteric surfactant; and in the present invention, there is no particular restriction, and thus any of them may be used provided that the surfactant is used in a usual cosmetic.

Illustrative example of the anionic surfactant includes a fatty acid soap such as sodium stearate and triethanolamine palmitate, an alkyl ether carboxylic acid and a slat thereof, a salt of a condensation product between an amino acid and a fatty acid, an alkane sulfonate salt, an alkene sulfonate salt, a sulfonate salt of a fatty acid ester, a sulfonate salt of a fatty acid amide, a sulfonate salt of a formalin condensate, an alkyl sulfonate ester salt, a sulfonate ester salt of a secondary higher alcohol, a sulfate ester salt of an alkyl and an allyl ether, a sulfate salt of a fatty acid ester, a sulfate ester salt of a fatty acid alkyrolamide, a sulfate ester salt of a Turkey red oil and so on, an alkyl phosphate salt, an ether phosphate salt, an alkyl ally ether phosphate salt, an amide phosphate salt, an N-acyl lactate salt, an N-acylsarcosinate salt, and an N-acylamino acid activator.

Illustrative example of the cationic surfactant includes an alkyl amine salt, an amine salt such as a fatty acid derivative of polyamine or a fatty acid derivative aminoalcohol, an alkyl quaternary ammonium salt, an aromatic quaternary ammonium salt, a pyridinum salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a methyl glucoside fatty acid ester, an alkyl polyglucoside, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethelene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytostanol ether, a polyoxyethylene phytosterol ether, a polyoxyethylene cholestanol ether, a polyoxyethylene cholesteryl ether, a linear or a branched polyoxyalkylene-modified organopolysiloxane, a linear or a branched organopolysiloxane co-modified with a polyoxyalkylene and an alkyl, a linear or a branched polyglycerin-modified organopolysiloxane, a linear or a branched organopolysiloxane co-modified with polyglycerin and an alkyl, an alkanol amide, a sugar ether, and a sugar amide.

Illustrative example of the amphoteric surfactant includes a betaine, phosphatidylcholine, an aminocarboxylic acid salt, an imidazoline derivative, and an amide amine type. Among these surfactants, a linear or a branched organopolysiloxane having a polyoxyalkylene chain or a polyglycerin chain in its molecular structure, or the linear or the branched organopolysiloxane further having a long chain alkyl group having 6 to 20 carbon atoms is preferable.

In these surfactants, amount of a hydrophilic polyoxyalkylene group or a hydrophilic polyglycerin group is preferably 10 to 70% by mass in its molecular structure; and in addition, amount thereof to be blended in a cosmetic is preferably 0.1 to 20% by mass, or particularly preferably 0.2 to 10% by mass, relative to the totality of the cosmetic.

(Silicone Resin)

The cosmetic of the present invention may contain, depending on the purpose thereof, one or two or more silicone resins selected from an acryl silicone resin and a net-work silicone resin. The acryl silicone resin is a graft or a block copolymer of an acryl and a silicone. It is also possible to use an acryl silicone resin containing in its molecular structure at least one kind selected from the group consisting of a pyrrolidinyl group, a long chain alkyl group, a polyoxyalkylene group, a fluoroalkyl group, and an anionic group such as a carboxyl group.

The net-work silicone resin is selected from a resin composed of a $R_3SiO_{0.5}$ unit and a $SiO_2$ unit; a resin composed of a $R_3SiO_{0.5}$ unit, a $R_2SiO$ unit, and a $SiO_2$ unit; a resin composed of a $R_3SiO_{0.5}$ unit and a $RSiO_{1.5}$ unit; a resin composed of a $R_3SiO_{0.5}$ unit, a $R_2SiO$ unit, and a $RSiO_{1.5}$ unit; and a resin composed of a $R_3SiO_{0.5}$ unit, a $R_2SiO$ unit, a $RSiO_{1.5}$ unit, and a $SiO_2$ unit. Here, R represents an organic group. It is also possible to use a net-work silicone containing in its molecular structure at least one kind selected from the group consisting of a pyrrolidinyl group, a long chain alkyl group, a polyoxyalkylene group, a fluoroalkyl group, and an amino group. When these silicone resins are used, amount thereof to be blended into a cosmetic is preferably 0.1 to 20% by mass, or more preferably 1 to 10% by mass, relative to the totality of the cosmetic.

(Composition Comprising a Crosslinking Organopolysiloxane and an Oil Material that is a Liquid at Room Temperature)

The cosmetic of the present invention may also use, depending on the purpose thereof, one or two or more kinds of a composition comprising a crosslinking organopolysiloxane and an oil material that is a liquid at room temperature. It is preferable that this crosslinking organopolysiloxane swell by absorbing the liquid oil the amount of which is more than own weight of the crosslinking organopolysiloxane. Here, the liquid oil such as the above-mentioned silicone oil, hydrocarbon oil, ester oil, natural plant and animal oil, semi-synthetic oil, and fluorine oil may be used; and illustrative example thereof includes a low viscous silicone oil having viscosity of 0.65 to 100.0 $mm^2$/second (at 25° C.); a hydrocarbon oil such as a liquid paraffin, squalane, isododecane, and isohexadecane; a glyceride oil such as trioctanoin; an ester oil such as isotridecyl isononanoate, an N-acyl glutamate ester, and lauroyl sarocosinate; and a natural plant and animal oil such as a macademia nut oil. It is preferable that the crosslinking agent of this crosslinking organopolysiloxane have two or more reactive vinyl moieties in its molecular structure and form a crosslinking structure by reacting with a hydrogen atom directly bonded to a silicon atom. Illustrative example of the crosslinking agent having two or more reactive vinyl moieties in its molecular structure includes an organopolysiloxane containing two or more vinyl groups in its molecular structure, a polyoxyalkylene containing two or more allyl groups in its molecular structure, a polyglycerin containing two or more allyl groups in its molecular structure, and an $\alpha,\omega$-alkenyl diene. Further, a crosslinking agent containing at least one kind selected from the group consisting of a polyoxyalkylene group, a polyglycerin moiety, a long chain alkyl group, an alkenyl group, an aryl group, and a fluoroalkyl group, can be used. Amount of the composition comprising the crosslinking organopolysiloxane and the oil material that is a liquid at room temperature is, if it is used, preferably 0.1 to 80% by mass, or more preferably 1 to 50% by mass, relative to the totality of the cosmetic.

(Silicone-Modified Olefin Wax)

The cosmetic of the present invention may contain, depending on the purpose thereof, one or two or more kinds of a silicon-modified olefin wax obtained by an addition reaction of an olefin wax, obtained by reacting an $\alpha$-olefin and diene and containing an unsaturated group, with an organohydrogen polysiloxane containing one or more SiH bond in its molecular structure. As to the $\alpha$-olefin, those having 2 to 12 carbon atoms such as ethylene, propylene, 1-butene, 1-hexene, and 4-methyl-1-pentene are preferable; and as to the diene, butadiene, isoprene, 1,4-hexadiene, vinyl norbornene, ethylidene norbornene, dicyclopentadiene, and so on are preferable. As to the organohydrogen polysiloxane containing the SiH bond, those having a linear structure, a siloxane branched structure, and so on may be used.

(Other Additive Components)

The cosmetic of the present invention may be added with a component generally used in a usual cosmetic in the amount without adversely affecting the effects of the present invention; illustrative example thereof includes an oil-soluble gelation agent, an organic-modified clay mineral, an antiperspirant, a UV-absorber, a UV absorbing-scattering agent, a moisturizer, an antibacterial preservative, an antibacterial agent, a fragrance, a salt, an antioxidant, a pH controller, a chelating agent, an algefacient, an anti-inflammatory agent, a skin care component (a skin-lightening agent, a cell activator, a rough-skin improver, a blood circulation promoter, a skin astringent agent, an antiseborrheic agent, and so on), a vitamin, an amino acid, a nucleic acid, a hormone, a clathrate compound, and a hair-immobilizing agent.

Illustrative example of the oil-soluble gelation agent is selected from the gelation agents including a metal soap such as aluminum stearate, magnesium stearate, and zinc myristate; an amino acid derivative such as N-lauroyl-L-glutamic acid and $\alpha,\gamma$-di-n-butyl amine; a dextrin fatty acid ester such as dextrin palmitate ester, dextrin stearate ester, and dextrin 2-ethylhexanoate palmitate ester; a sucrose fatty acid ester such as sucrose palmitate ester and sucrose stearate ester; a fructo-oligosaccharide fatty acid ester such as fructo-oligosaccharide stearate ester and fructo-oligosaccharide 2-ethylhexanoate ester; a benzylidene derivative of sorbitol such as monobenzylidene sorbitol and dibenzylidene sorbitol; an organic-modified clay mineral such as dimethyl benzyl dodecyl ammonium montomorillonite clay and dimethyl dioctadecyl ammonium montomorillonite clay.

Illustrative example of the antiperspirant is selected from the antiperspirants including aluminum chlorohydrate, aluminum chloride, aluminum sesquichlorohydrate, zirconyl hydroxy chloride, aluminum zirconium hydroxy chloride, and aluminum zirconium glycine complex.

Illustrative example of the UV-absorber includes a benzoic acid UV-absorber such as para-amino benzoic acid; an anthranilic acid UV-absorber such as methyl anthranilate; a salicylic acid UV-absorber such as methyl salicylate, octyl salicylate, and trimethylcyclohexyl salicylate; a cinnamic acid UV-absorber such as octyl para-methoxy cinnamate; a benzophenone UV-absorber such as 2,4-dihydroxybenzophenone; a urocanic acid UV-absorber such as ethyl urocanate; a dibenzoylmethane UV-absorber such as 4-t-butyl-4'-methoxy-dibenzoylmethane; phenyl benzimidazole sulfonic acid; and a triazine derivative. Illustrative example of the UV absorbing-scattering agent includes a particle, which absorbs and scatters a UV-beam, such as a titanium oxide microparticle, titanium oxide containing an iron microparticle, a zinc oxide microparticle, a cerium oxide microparticle, and a composite material of them. A dispersed material obtained by dispersing the particle, which absorbs and scatters a UV-beam, into an oil material prior to use may also be used.

Illustrative example of the moisturizer includes glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate salt, polyoxyethylene methyl glucoside, polyoxypropylene methyl glucoside, egg yolk lecithin, soybean lecithin, phosphatidyl choline, phosphatidyl ethanolamine, phosphatidyl serine, phosphatidyl glycerol, phosphatidyl inositol, and sphingo phospholipid.

Illustrative example of the antibacterial preservative includes a para-oxybenzoate alkyl ester, benzoic acid, sodium benzoate, sorbic acid, potassium sorbate, and phenoxy ethanol. Illustrative example of the antibacterial agent includes benzoic acid, salicylic acid, carbolic acid, sorbic acid, a para-oxybenzoate alkyl ester, p-chloro-m-cresol, hexachlorophene, benzalkonium chloride, chlorhexidine chloride, trichlorocarbanilide, a photosensitive element, and phenoxy ethanol.

Illustrative example of the fragrance includes an extracted liquid of an aloe, a turmeric, an oolong tea, an olive, an orange, a licorice, a raspberry, a cassia, a salvia, a perilla herb, a peony, a carrot, a loguat, a safflower, a peppermint, a peach, a lime, a lavender, a green tea, a rosemary, a royal jelly, and a wild thyme.

As to the salt, an inorganic salt, an organic salt, an amine salt, and an amino acid salt may be mentioned. Illustrative example of the inorganic salt includes a sodium salt, a potassium salt, a magnesium salt, a calcium salt, an aluminum salt, a zirconium salt, and a zinc salt of an inorganic acid such as hydrochloric acid, sulfuric acid, carbonic acid, and nitric acid. Illustrative example of the organic salt includes a salt of an organic acid such as acetic acid, dehydroacetic acid, citric acid, malic acid, succinic acid, ascorbic acid, and stearic acid. Illustrative example of the amine salt and amino acid salt includes a salt of an amine such as triethanol amine and an amino acid salt such as a glutamate salt. In addition, a salt of hyaluronic acid and chondroitin sulfate, an aluminum zirconium glycine complex, and a neutralized salt obtained by neutralization of an acid and a base used in a cosmetic prescription may be used. Illustrative example of the antioxidant includes tocopherol, p-t-butylphenol, butyl hydroxy anisole, dibutyl hydroxy toluene, and phytin. Illustrative example of the pH-controller includes lactic acid, citric acid, glycolic acid, succinic acid, tartaric acid, dl-malic acid, potassium carbonate, sodium bicarbonate, and ammonium bicarbonate. Illustrative example of the chelating agent includes alanine, sodium edetate, sodium polyphosphate, sodium metaphosphate, and phosphoric acid. Illustrative example of the algefacient includes L-menthol and camphor. Illustrative example of the anti-inflammatory agent includes allantoin, glycyrrhizic acid and its salt, glycyrrhetic acid, stearyl glycyrrhetinate, tranexamic acid, and azulene.

Illustrative example of the skin care component includes a skin-lightening agent such as a placenta extract, arbutin, glutathione, and a saxifrage extract; a cell activator such as a royal jelly, a photosensitive element, a cholesterol derivative, and an extract from hemolysed blood of a young calf; a rough-skin improver; a blood circulation promoter such as nonylic acid warenylamide, benzyl nicotinate ester, β-butoxyethyl nicotinate ester, capsaicin, zingerone, cantharides tincture, ichthammol, caffeine, tannic acid, α-borneol, nicotinic acid tocopherol, inositol hexanicotinate, cyclandelate, cinnarizine, tolazoline, acetyl choline, verapamil, cepharanthin, and γ-orizanol; a skin astringent agent such as zinc oxide and tannic acid; and an antiseborrheic agent such as sulfur and thianthrol.

Illustrative example of the vitamin includes a vitamin A such as a vitamin A oil, retinol, retinol acetate, and retinol palmitate; a vitamin B including a vitamin $B_2$ such as riboflavin, riboflavin butyrate, and a flavin adenine nucleotide, a vitamin $B_6$ such as pyridoxine hydrochloride salt, pyridoxine dioctanoate, and pyridoxine tripalmitate, a vitamin $B_{12}$ and its derivative, and vitamin $B_{15}$ and its derivative; a vitamin C such as L-ascorbic acid, L-ascorbic acid dipalmitate ester, sodium L-ascorbic-2-sulfate, and dipotassium L-ascorbic acid phosphate diester; a vitamin D such as ergocalciferol and cholecalciferol; a vitamin E such as α-tocopherol, β-tocopherol, γ-tocopherol, dl-α-tocopherol acetate, dl-α-tocopherol nicotinate, and dl-α-tocopherol succinate; a vitamin H; a vitamin P; a nicotinic acid such as nicotinic acid, benzyl nicotinate, and a nicotinic acid amide; a pantothenic acid such as calcium pantothenate, D-pantothenyl alcohol, pantothenyl ethyl ether, and acetyl pantothenyl ethyl ether; and biotin.

Illustrative example of the amino acid includes glycine, valine, leucine, isoleucine, serine, threonine, phenylalanine, arginine, lysine, aspartic acid, glutamic acid, cystine, cysteine, methionine, and tryptophan. Illustrative example of the nucleic acid includes deoxyribonucleic acid. Illustrative example of the hormone includes estradiol and ethinyl estradiol.

Illustrative example of the clathrate compound includes cyclodextrin and a crown ether.

As to the hair-immobilizing polymer, an amphoteric polymer, an anionic polymer, a cationic polymer, and a nonionic polymer may be mentioned. Illustrative example of the hair-immobilizing polymer includes a polyvinyl pyrrolidone polymer such as polyvinyl pyrrolidone and vinyl pyrrolidone/vinyl acetate copolymer; an acidic vinyl ether polymer such as methyl vinyl ether/maleic anhydride alkyl half-ester copolymer; an acidic polyvinyl acetate polymer such as vinyl acetate/crotonic acid copolymer; an acidic acryl polymer such as a (meth)acrylic acid/alkyl (meth)acrylate copolymer and a (meth)acrylic acid/alkyl (meth)acrylate/alkyl acrylamide copolymer; and an amphoteric acryl polymer such as a N-methacryloylethyl-N,N-dimethyl ammonium/α-N-methylcarboxybetaine/alkyl (meth)acrylate copolymer and hydroxypropyl (meth)acrylate/butylaminoethyl methacrylate/acrylic acid octyl amide copolymer. In addition, a polymer derived from a nature such as cellulose or its derivative, and keratin and collagen or a derivative thereof may be used suitably.

In the present invention, the form or the configuration of the cosmetic is not particularly restricted; and thus, any of a water-base, an oil-base, a water-in-oil emulsion, an oil-in-water emulsion, a non-aqueous emulsion, a multi-emulsion such as W/O/W (water/oil/water) and O/W/O (oil/water/oil), a suspension, a paste, and a solid may be used.

The cosmetic may be arbitrarily applied. The application thereof includes a skin care cosmetic such as a beauty lotion, a milky lotion, a cream, a cleansing cream, a pack, an oil liquid, a massage material, a liquid cosmetic, an beauty oil, a hand cream, a lip cream, and a wrinkle concealer; a make-up cosmetic such as a make-up foundation, a concealer, a white powder, a powder foundation, a liquid foundation, a cream foundation, an oil foundation, a rouge, an eye shadow, a mascara, an eye liner, an eye blow, and a lipstick; a hair cosmetic such as a shampoo, a rinse, a treatment, and a setting material; a UV-protective cosmetic such as a sunscreen oil, a sunscreen lotion, and a sunscreen cream; and a cleaning cosmetic, a deodorant, an antiperspirant, and so on.

EXAMPLES

Hereinafter, the present invention will be explained in more detail by showing Synthesis Examples of the organopolysiloxane of the present invention and Examples of the cosmetic of the present invention; but the present invention is not limited to them.

Synthesis Example 1

Into a reactor were charged 35.3 parts by mass of an addition compound of total 9 moles of ethylene oxide per one mole of triglycerin diallyl ether shown by the following average formula (7),

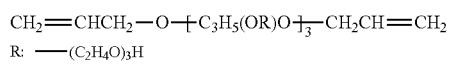
(7)

R: ——(C₂H₄O)₃H 456 parts by mass of a polysiloxane having hydrogen on its one end shown by the following formula (8), and

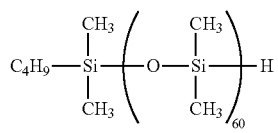
(8)

500 parts by mass of isopropyl alcohol; and after 0.5 parts by mass of the toluene solution containing 0.5% by mass of chloroplatinic acid was added thereinto, the resulting mixture was reacted under reflux for two hours. Thereafter, the reaction solution was heated under reduced pressure to distill the solvent out to obtain an organopolysioxane containing a polyoxyethylene group shown by the following formula (9).

propylene oxide per one mole of pentaglycerin diallyl ether shown by the following average formula (10),

CH₂=CHCH₂—O—(C₃H₅(OR)O)₅—CH₂CH=CH₂    (10)

R: ——(C₂H₄O)₂(C₃H₆O)₂H 376 parts by mass of a polysiloxane having hydrogen on its one end shown by the following formula (11), and

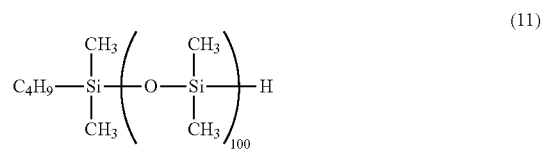
(11)

500 parts by mass of isopropyl alcohol; and after 0.5 parts by mass of the toluene solution containing 0.5% by mass of chloroplatinic acid was added thereinto, the resulting mixture was reacted under reflux for two hours. Thereafter, the reaction solution was heated under reduced pressure to distill the solvent out to obtain an organopolysioxane containing a polyoxyethylene-polyoxypropylene group shown by the following formula (12).

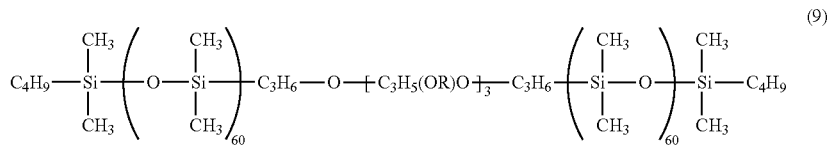
(9)

R: ——(C₂H₄O)₃H

Synthesis Example 2

Into a reactor were charged 37.2 parts by mass of an addition compound of 10 moles of ethylene oxide and 10 moles of

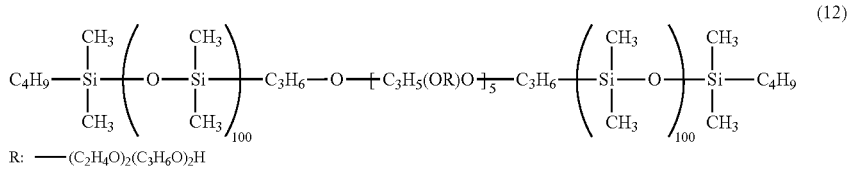
(12)

R: ——(C₂H₄O)₂(C₃H₆O)₂H

Synthesis Example 3

Into a reactor were charged 41.5 parts by mass of an addition compound of total 9 moles of ethylene oxide per one mole of tetraglycerin triallyl ether shown by the following average formula (13),

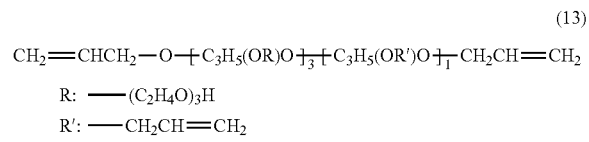

R: —(C₂H₄O)₃H
R': —CH₂CH=CH₂

240 parts by mass of a polysiloxane having hydrogen on its one end shown by the following formula (14), and

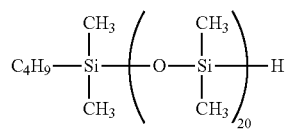

300 parts by mass of isopropyl alcohol; and after 0.3 parts by mass of the toluene solution containing 0.5% by mass of chloroplatinic acid was added thereinto, the resulting mixture was reacted under reflux for two hours. Thereafter, the reaction solution was heated under reduced pressure to distill the solvent out to obtain an organopolysioxane containing a polyoxyethylene group shown by the following formula (15).

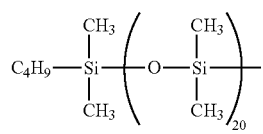

R: —(C₂H₄O)₃H

Synthesis Example 4

Into a reactor were charged 63.4 parts by mass of an addition compound of 20 moles of ethylene oxide and 3 moles of butylene oxide per one mole of monoglycerin diallyl ether shown by the following average formula (16),

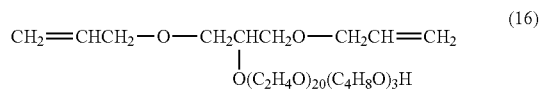

456 parts by mass of a polysiloxane having hydrogen on its one end shown by the formula (8), and 500 parts by mass of isopropyl alcohol; and after 0.5 parts by mass of the toluene solution containing 0.5% by mass of chloroplatinic acid was added thereinto, the resulting mixture was reacted under reflux for two hours. Thereafter, the reaction solution was heated under reduced pressure to distill the solvent out to obtain an organopolysioxane containing a polyoxyethylene-polyoxybutylene group shown by the following formula (17).

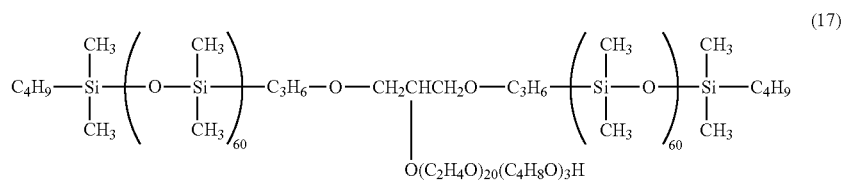

Synthesis Example 5

Into a reactor were charged 35.8 parts by mass of an addition compound of total 9 moles of ethylene oxide per one mole of triglycerin diallyl ether shown by the formula (7), 306 parts by mass of a polysiloxane having hydrogen on its one end shown by the following formula (18), and

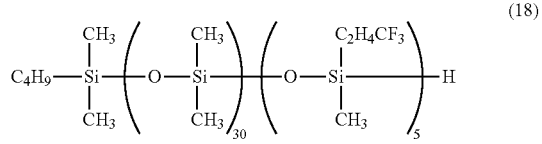

300 parts by mass of isopropyl alcohol; and after 0.3 parts by mass of the toluene solution containing 0.5% by mass of chloroplatinic acid was added thereinto, the resulting mixture was reacted under reflux for two hours. Thereafter, the reaction solution was heated under reduced pressure to distill the solvent out to obtain an organopolysioxane containing a polyoxyethylene group shown by the following formula (19).

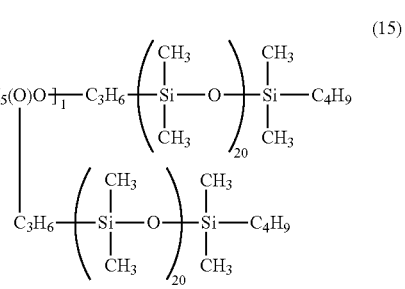

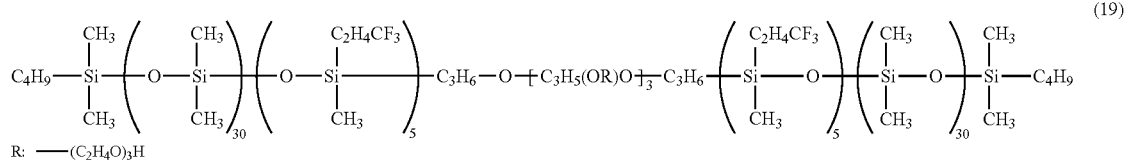

(19)

Synthesis Example 6

Into a reactor were charged 44.6 parts by mass of an addition compound of 10 moles of ethylene oxide and 10 moles of propylene oxide per one mole of pentaglycerin diallyl ether shown by the formula (10), 348 parts by mass of a polysiloxane having hydrogen on its one end shown by the following formula (20), and

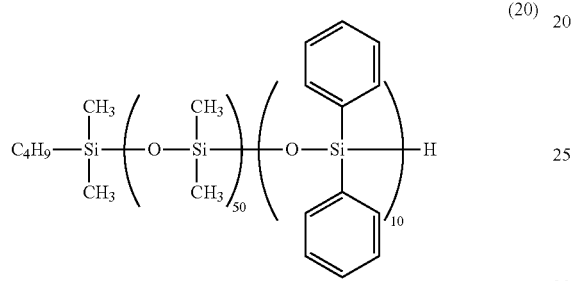

(20)

300 parts by mass of isopropyl alcohol; and after 0.3 parts by mass of the toluene solution containing 0.5% by mass of chloroplatinic acid was added thereinto, the resulting mixture was reacted under reflux for two hours. Thereafter, the reaction solution was heated under reduced pressure to distill the solvent out to obtain an organopolysioxane containing a polyoxyethylene-polyoxypropylene group shown by the following formula (21).

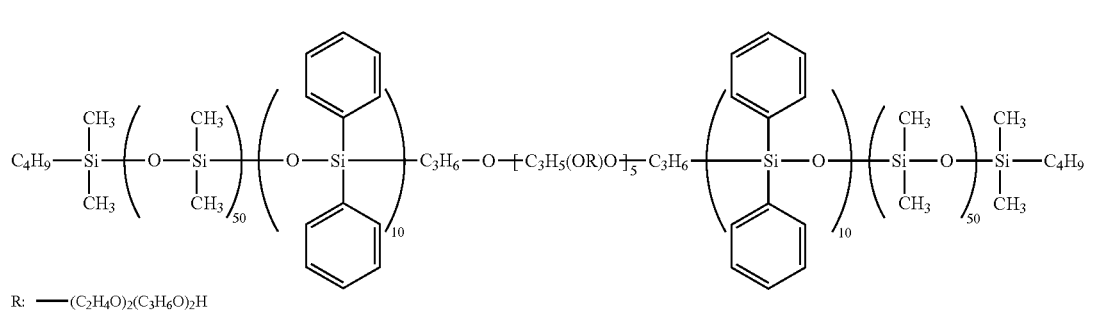

(21)

Examples 1 to 3 and Comparative Examples 1 to 2

Each of the W/O emulsions with the composition shown in Table 1 (amount of blending is based on % by mass) was prepared by the method shown below; and temporal stability thereof was evaluated.

(Preparation Method)

The following components 1 to 6 were mixed by agitation with a dispersion mixer at 1500 rpm, and then components 7 and 8 were gradually added thereto for emulsification.

(Evaluation Method)

After 100 g of the emulsion thus obtained was allowed to stand in a sealed container at 50° C. for one week, temporal stability was evaluated according to the following criteria by visual observation as to the emulsion state thereof.
(Evaluation Criteria)
Good: No separation was observed.
Fair: Slight separation was observed.
Bad: Separation into two phases was observed.

(Preparation Method)
A: Components 1 to 7 were mixed with heating; and then components 8 to 14 were added thereinto and mixed uniformly.
B: Components 15, 16, and component 18 were dissolved by heating.

TABLE 1

| | Amount of blending (parts by mass) | | | | |
|---|---|---|---|---|---|
| Components | Example 1 | Example 2 | Example 3 | Comparative Example 1 | Comparative Example 2 |
| 1 Dimethyl polysiloxane (6 mm²/second) | 20 | 20 | 20 | 20 | 20 |
| 2 Organopolysiloxane of Synthesis Example 1 | 2 | — | — | — | — |
| 3 Organopolysiloxane of Synthesis Example 2 | — | 2 | — | — | — |
| 4 Organopolysiloxane of Synthesis Example 3 | — | — | 2 | — | — |
| 5 Organopolysiloxane shown by below structure (note 1) | — | — | — | 2 | — |
| 6 Organopolysiloxane shown by below structure (note 2) | — | — | — | — | 2 |
| 7 1,3-Butylene glycol | 5 | 5 | 5 | 5 | 5 |
| 8 Purified water | 73 | 73 | 73 | 73 | 73 |
| Stability after one week at 50° C. | Good | Good | Good | Fair | Fair |

(note 1):
Organopolysiloxane shown by the following formula.

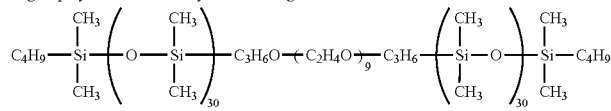

(note 2):
Organopolysiloxane shown by the following formula.

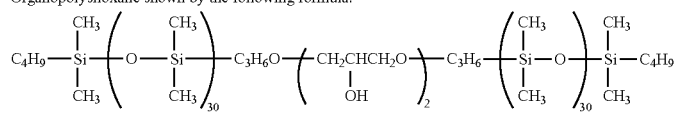

As shown in table 1, emulsions using Synthesis Examples 1 to 3 (Examples 1 to 3) kept the initial emulsion state thereof even after one week at 50° C., while the emulsions of Comparative Examples 1 to 2 was lacking temporal stability, because the oil phases thereof were not fully uniform.

Examples 4 to 6 and Comparative Examples 3 to 4

Each of the W/O foundations was prepared by using respective organopolysiloxanes obtained in Synthesis Examples 1 to 3; and then, temporal stability and characteristics thereof (usability (use feeling), uniformity of color tone, and cosmetic sustainability (cosmetic durability)) were evaluated.

C: With agitation, B was gradually added into A for emulsification; and then, after cooling, component 17 was added to the emulsion to obtain a foundation.
(Evaluation Method)
After 100 g of the foundation thus obtained was allowed to stand in a sealed container at 50° C. for one month, temporal stability was evaluated according to the following criteria by visual observation as to the emulsion state and pigment dispersion state thereof.
(Evaluation Criteria)
Good: No separation was observed.
Fair: Slight separation was observed.
Bad: Separation into two phases was observed.

TABLE 2

| | | Amount of blending (parts by mass) | | | | |
|---|---|---|---|---|---|---|
| | Components | Example 4 | Example 5 | Example 6 | Comparative Example 3 | Comparative Example 4 |
| 1 | Decamethyl cyclopentasiloxane | 45 | 45 | — | 45 | 45 |
| 2 | Dimethyl polysiloxane | 5 | 5 | — | 5 | 5 |
| 3 | Organopolysiloxane of Synthesis Example 1 | 2 | — | — | — | — |
| 4 | Organopolysiloxane of Synthesis Example 2 | — | 2 | — | — | — |
| 5 | Organopolysiloxane of Synthesis Example 3 | — | — | 2 | — | — |
| 6 | Organopolysiloxane (note 1) | — | — | — | 2 | — |
| 7 | Organopolysiloxane (note 2) | — | — | — | — | 2 |

TABLE 2-continued

| Components | Amount of blending (parts by mass) | | | | |
|---|---|---|---|---|---|
| | Example 4 | Example 5 | Example 6 | Comparative Example 3 | Comparative Example 4 |
| 8 Montomorillonite modified with octadecyl dimethyl benzyl ammonium salt | 4 | 4 | 4 | 4 | 4 |
| 9 Hydrophobized titanium oxide (note 3) | 10 | 10 | 10 | 10 | 10 |
| 10 Hydrophobized talc (note 3) | 6 | 6 | 6 | 6 | 6 |
| 11 Hydrophobized mica (note 3) | 6 | 6 | 6 | 6 | 6 |
| 12 Hydrophobized red iron oxide (note 3) | 1.6 | 1.6 | 1.6 | 1.6 | 1.6 |
| 13 Hydrophobized yellow iron oxide (note 3) | 0.7 | 0.7 | 0.7 | 0.7 | 0.7 |
| 14 Hydrophobized black iron oxide (note 3) | 0.2 | 0.2 | 0.2 | 0.2 | 0.2 |
| 15 Dipropylene glycol | 5 | 5 | 5 | 5 | 5 |
| 16 p-Oxybenzoate methyl ester | 0.3 | 0.3 | 0.3 | 0.3 | 0.3 |
| 17 Fragrance | Appropriate | Appropriate | Appropriate | Appropriate | Appropriate |
| 18 Water | Remainder | Remainder | Remainder | Remainder | Remainder |
| Stability after one month at 50° C. | Good | Good | Good | Fair | Fair |

(note 1) and (note 2) are the same as before.
(note 3)
(hydrophobic treatment): heat treatment of the powder was done after methyl hydrogen polysiloxane with the amount thereof being 2% relative to the powder was added to the powder.

As shown in Table 2, foundations using Synthesis Examples 1 to 3 (Examples 4 to 6) kept the initial emulsion state thereof even after one month at 50° C., while the foundations of Comparative Examples 1 to 2 was lacking temporal stability, and because powder-dispersion stability thereof was not enough.

Then, the use test was done by 50 women expert panelists on the foundations obtained in Examples 4 to 6 and Comparative Examples 3 to 4; the usability (use feeling), uniformity of color tone, and cosmetic sustainability were evaluate according to the following criteria. evaluation results are shown in Table 3.

(Evaluation Criteria)

On each evaluation item, an average score of the panelists' total scores was calculated.

5 Point: Excellent
4 Point: Good
3 Point: Fair
2 Point: Poor
1 Point: Bad

Evaluation in Table 3 was made based on the following criteria.

Obtained average score of 4.5 or more: Excellent
Obtained average score of 3.5 or more and less than 4.5: Good
Obtained average score of 2.5 or more and less than 3.5: Fair
Obtained average score of 1.5 or more and less than 2.5: Poor
Obtained average score of less than 1.5: Bad

TABLE 3

| | Example 4 | Example 5 | Example 6 | Comparative Example 3 | Comparative Example 4 |
|---|---|---|---|---|---|
| Usability | Excellent | Excellent | Good | Fair | Good |
| Uniformity of color tone | Excellent | Excellent | Excellent | Good | Good |
| Cosmetic sustainability | Excellent | Good | Excellent | Fair | Fair |

As shown in Table 3, the foundations in Comparative Examples 3 and 4 showed good color tone during the time of application; but skin affinity (skin-contact property) was weak and cosmetic sustainability (cosmetic durability) was insufficient. On the contrary, the foundations in Examples 4 to 6 showed good usability and pigment dispersion; and thus, a foundation with high fineness, uniform color tone, excellent skin affinity, and good cosmetic sustainability could be obtained.

In the following Examples, temporal stability was confirmed as to whether or not there was a change in appearance after the cosmetic was allowed to stand in a sealed container at 50° C. for one month.

Example 7

Eye Liner

| (Components) | (%) |
|---|---|
| 1. Octamethyl cyclotetrasiloxane | remainder |
| 2. Organopolysiloxane of Synthesis Example 6 | 3.0 |
| 3. Silicone resin (note 1) | 15.0 |
| 4. Montomorillonite modified with dioctadecyl dimethyl ammonium salt | 3.0 |
| 5. Silicone-treated black iron oxide (note 2) | 10.0 |
| 6. 1,3-Butylene glycol | 5.0 |
| 7. Preservative | appropriate amount |
| 8. Fragrance | appropriate amount |
| 9. Purified water | 10.0 |

(note 1)
(silicone resin): 50%-D5 solution of a net-work silicone compound with the ratio [Me$_3$SiO$_{1/2}$]/[SiO$_2$] being 0.8 (Me represents a methyl group).
(note 2)
(silicone-treated black iron oxide): black iron oxide was heat-treated with 2% by mass (relative to the black iron oxide) of methyl hydrogen polysiloxane at 150° C.

(Preparation Method)

A: Components 1 to 4 were mixed; and after component 5 was added thereinto, they were uniformly mixed and dispersed.

B: Components 6 to 7 and component 9 were mixed.

C: The mixture obtained in B was gradually added into the dispersed mixture obtained in A for emulsification; and then component 8 was added into this emulsified mixture to obtain the eye liner.

(Evaluation)

The eye liner thus obtained had light spreading property and thus was easy to draw; and in addition, it showed no stickiness and was excellent in cosmetic sustainability without any change by temperature and passage of time.

Example 8

Suntan Cream

| (Components) | (%) |
|---|---|
| 1. Decamethyl cyclopentasiloxane | 15.0 |
| 2. Dimethyl polysiloxane (100 mm$^2$/second) | 5.0 |
| 3. Silicone wax | 0.5 |
| 4. Organopolysiloxane of Synthesis Example 3 | 6.0 |
| 5. Palmitic acid | 0.2 |
| 6. Dimethyloctyl para-aminobenzoate | 0.5 |
| 7. 4-t-Butyl-4'-methoxy-dibenzoyl methane | 0.5 |
| 8. Kaolin | 0.5 |
| 9. Red iron oxide | 0.2 |
| 10. Yellow iron oxide | 0.3 |
| 11. Black iron oxide | 0.1 |
| 12. Mica coated with titanium oxide | 1.0 |
| 13. Sodium L-glutamate | 3.0 |
| 14. 1,3-Butylene glycol | 5.0 |
| 15. Dioctadecyl dimethyl ammonium chloride | 0.1 |
| 16. Anti-oxidant | appropriate amount |
| 17. Preservative | appropriate amount |
| 18. Fragrance | appropriate amount |
| 19. Purified water | remainder |

(Preparation Method)

A: Components 1 to 7 and components 16 to 17 were dissolved by heating.

B: Component 15 and a part of component 19 were heated with agitation; and after components 8 to 12 were added thereinto, the resulting mixture was dispersed.

C: Components 13 to 14 and the rest of component 19 were dissolved, and then they were mixed with the dispersed mixture obtained in B.

D: The dispersed mixture obtained in C was gradually added into the mixture obtained in A with agitation for emulsification; and then, after cooling, component 18 was added into this emulsified mixture to obtain the suntan cream.

(Evaluation)

The suntan cream thus obtained was highly fine with wide and light spreading properties without stickiness, and gave a vivid and refreshing use feeling with good temporal stability and cosmetic sustainability.

Example 9

Cream

| (Components) | (%) |
|---|---|
| 1. Decamethyl cyclopentasiloxane | 20.0 |
| 2. Glyceryl trioctanoate | 10.0 |
| 3. Organopolysiloxane of Synthesis Example 2 | 4.0 |
| 4. Phenyl dimethyl stearyl ammonium chloride | 1.0 |
| 5. Dipropylene glycol | 10.0 |
| 6. Maltitol | 10.0 |
| 7. Saponite | 1.5 |
| 8. Preservative | appropriate amount |
| 9. Fragrance | appropriate amount |
| 10. Purified water | remainder |

(Preparation Method)

A: Components 1 to 4 and component 8 were mixed with heating.

B: Components 5 to 7 and component 10 were dissolved by heating.

C: The solution obtained in B was gradually added into the mixture obtained in A with agitation for emulsification; and then, after cooling, component 9 was added into this emulsified mixture to obtain the cream.

(Evaluation)

The cream thus obtained showed wide and light spreading properties without stickiness and greasiness, and gave a vivid and refreshing use feeling with good temporal stability.

Example 10

Sunscreen Cream

| (Components) | (%) |
|---|---|
| 1. Decamethyl cyclopentasiloxane | 20.0 |
| 2. Liquid paraffin | 10.0 |
| 3. Organopolysiloxane of Synthesis Example 1 | 4.0 |
| 4. 4-t-Butyl-4'-methoxy dibenzoyl methane | 7.0 |
| 5. Distearyl dimethyl ammonium chloride | 0.8 |
| 6. Vitamin E acetate | 0.1 |
| 7. Ethanol | 1.0 |
| 8. Aluminum magnesium silicate | 1.2 |
| 9. Preservative | appropriate amount |
| 10. Fragrance | appropriate amount |
| 11. Purified water | remainder |

(Preparation Method)

A: Components 1 to 6 and component 9 were mixed with heating.

B: Components 7 to 8 and component 11 were mixed and dispersed uniformly with heating.

C: The dispersed mixture obtained in B was gradually added into the mixture obtained in A with agitation for emulsification; and then, after cooling, component 10 was added into this emulsified mixture to obtain the sunscreen cream.

(Evaluation)

The sunscreen cream thus obtained was highly fine with wide and light spreading properties without temporal instability. The cream was not sticky and thus sands were not adhered to a skin at all; and thus, it was excellent in its usability. In addition, the UV-cut effect was durable because of good cosmetic sustainability.

Example 11

Eye Shadow

| (Components) | (%) |
| --- | --- |
| 1. Decamethyl cyclopentasiloxane | 15.0 |
| 2. Dimethyl polysiloxane (6 mm²/second) | 10.0 |
| 3. Organopolysiloxane of Synthesis Example 5 | 2.0 |
| 4. PEG (10) lauryl ether | 0.5 |
| 5. Silicone-treated chromium oxide (note 1) | 6.2 |
| 6. Silicone-treated ultramarine (note 1) | 4.0 |
| 7. Silicone-treated titanium-coated mica (note 1) | 6.0 |
| 8. Sodium chloride | 2.0 |
| 9. Propylene glycol | 8.0 |
| 10. Preservative | appropriate amount |
| 11. Fragrance | appropriate amount |
| 12. Purified water | remainder |

(note 1)
(silicone treatment): a powder was heat-treated with 3% by mass (relative to the powder) of methyl hydrogen polysiloxane at 150° C.

(Preparation Method)

A: Components 1 to 4 were mixed and then added with components 5 to 7; and they were dispersed uniformly.

B: Components 8 to 10 and component 12 were dissolved uniformly.

C: The solution obtained in B was gradually added into the dispersed mixture obtained in A with agitation for emulsification; and then, after cooling, component 11 was added into this emulsified mixture to obtain the eye shadow.

(Evaluation)

The eye shadow thus obtained had wide and light spreading properties with a vivid and refreshing use feeling without greasiness and powderiness. In addition, it was excellent in water-resistance, water-repellency, sweat-resistance, durability, and cosmetic sustainability. It showed excellent stability because there was no change with time and temperature.

Example 12

Lip Cream

| (Components) | (%) |
| --- | --- |
| 1. Decamethylcyclopentasiloxane | 40.0 |
| 2. Isoparaffin (boiling point of 155° C.) | 10.0 |
| 3. Squalane | 10.0 |
| 4. Lanolin | 2.0 |
| 5. Trimethylsiloxy silicate | 3.0 |
| 6. Microcrystalline wax | 3.0 |
| 7. Organopolysiloxane of Synthesis Example 6 | 3.0 |
| 8. Lauroylglutamic acid dibutylamide | 5.0 |
| 9. Sodium lactate | 0.3 |
| 10. Sodium L-glutamate | 0.3 |
| 11. Sodium hyaluronate | 0.1 |
| 12. Sorbitol | 0.5 |
| 13. Glycerin | 5.0 |
| 14. Red No. 202 | appropriate amount |
| 15. Menthol | appropriate amount |
| 16. Preservative | appropriate amount |
| 17. Fragrance | appropriate amount |
| 18. Purified water | remainder |

(Preparation Method)

A: Components 1 to 8 were mixed with heating.

B: Components 9 to 16 and component 18 were dissolved by heating.

C: The solution obtained in B was gradually added into the mixture obtained in A with agitation for emulsification; and then, after component 17 was added into this emulsified mixture, the resulting mixture was filled in a capsule to obtain the lip cream.

(Evaluation)

The solid, water-in-oil type lip cream thus obtained had wide and light spreading properties with a moist, vivid, and refreshing use feeling without stickiness and greasiness. In addition, the lip cream applied was excellent in temporal stability and sustainability.

Example 13

Liquid Milky Foundation

| (Components) | (%) |
| --- | --- |
| 1. Dimethyl polysiloxane (6 mm²/second) | 5.0 |
| 2. Decamethyl cyclopentasiloxane | 15.0 |
| 3. Squalane | 4.0 |
| 4. Neopentyl glycol dioctanoate | 3.0 |
| 5. Myristate isostearate diglyceride | 2.0 |
| 6. α-Monoisostearyl glyceryl ether | 1.0 |
| 7. Organopolysiloxane of Synthesis Example 1 | 1.0 |
| 8. Aluminum distearate salt | 0.2 |
| 9. Hydrophobized titanium oxide (note 1) | 5.0 |
| 10. Hydrophobized sericite (note 1) | 2.0 |
| 11. Hydrophobized talc (note 1) | 3.0 |
| 12. Hydrophobized red iron oxide (note 1) | 0.4 |
| 13. Hydrophobized yellow iron oxide (note 1) | 0.7 |
| 14. Hydrophobized black iron oxide (note 1) | 0.1 |
| 15. Magnesium sulfate | 0.7 |
| 16. Glycerin | 3.0 |
| 17. Preservative | appropriate amount |
| 18. Fragrance | appropriate amount |
| 19. Purified water | remainder |

(note 1)
(hydrophobized powder): a powder was treated with stearic acid, the amount thereof being 2% by mass (relative to the powder).

(Preparation Method)

A: Components 1 to 8 were mixed with heating, and then components 9 to 14 were mixed with them uniformly.

B: Components 15 to 17 and component 19 were dissolved by heating.

C: The solution obtained in B was gradually added into the mixture obtained in A with agitation for emulsification; and then, after cooling, component 18 was added into this emulsified mixture to obtain the liquid milky foundation.

(Evaluation)

The liquid milky foundation thus obtained was highly fine and low viscous while having wide and light spreading properties with a moist, vivid, and refreshing use feeling without stickiness and greasiness. In addition, it was excellent in temporal stability and cosmetic sustainability on a skin.

Example 14

Transparent Gel Cosmetic

| (Components) | (%) |
|---|---|
| 1. Decamethyl cyclopentasiloxane | 10.0 |
| 2. Organopolysiloxane of Synthesis Example 2 | 10.0 |
| 3. 1,3-Butylene glycol | 10.0 |
| 4. Polyethylene glycol 400 | 9.0 |
| 5. 2-hydroxyoctanoic acid | 1.0 |
| 6. Sorbitol (70% aqueous solution) | 10.0 |
| 7. Citric acid | appropriate amount |
| 8. Sodium citrate | appropriate amount |
| 9. Preservative | appropriate amount |
| 10. Fragrance | appropriate amount |
| 11. Purified water | remainder |

(Preparation Method)

A. Components 3 to 11 were dissolved uniformly.

B: Components 1 to 2 were mixed uniformly.

C: The solution obtained in A was gradually added into the mixture obtained in B with agitation for emulsification to obtain the transparent gel cosmetic.

(Evaluation)

The transparent gel cosmetic thus obtained had wide and light spreading properties with a moist, vivid, and refreshing use feeling and without stickiness and greasiness. In addition, it was excellent in skin-affinity and temporal stability.

Example 15

Sunscreen Beauty Lotion

| (Components) | (%) |
|---|---|
| 1. Decamethyl cyclopentasiloxane | 14.0 |
| 2. Organopolysiloxane of Synthesis Example 2 | 10.0 |
| 3. Squalane | 1.5 |
| 4. Octyl p-methoxycinnamate | 3.0 |
| 5. Hydrophobized titanium oxide superfine microparticle (note 1) | 2.0 |
| 6. 1,3-Butylene glycol | 10.0 |
| 7. Sodium chloride | 2.0 |
| 8. L-Proline | 0.1 |
| 9. 2-Hydoxyoctanoic acid | 1.0 |
| 10. 2-Hydoxypropanoic acid | 5.0 |
| 11. Sodium hydroxide | appropriate amount |
| 12. Preservative | appropriate amount |
| 13. Fragrance | appropriate amount |
| 14. Purified water | remainder |

(note 1)
(hydrophobized titanium oxide superfine microparticle): Titan TTO-V-4 (Manufactured by Ishihara Sangyo Kaisha, Ltd.)

(Preparation Method)

A: Components 6 to 14 were dissolved uniformly.

B: Components 1 to 4 were mixed, and then component 5 was added thereinto uniformly.

C: B was gradually added into A with agitation and they were emulsified to obtain the sunscreen beauty lotion.

(Evaluation)

The sunscreen beauty lotion thus obtained had wide and light spreading properties with a moist, vivid, and refreshing use feeling and without stickiness and greasiness. In addition, it was excellent in skin-affinity and temporal stability with good sunscreen effect.

Example 16

Milky Lotion

| (Components) | (%) |
|---|---|
| 1. Decamethyl cyclopentasiloxane | 18.0 |
| 2. Dimethyl polysiloxane (6 mm$^2$/second) | 6.0 |
| 3. Squalane | 5.0 |
| 4. Neopentyl glycol dioctanoate | 3.0 |
| 5. α-Monooleyl glyceryl ether | 1.0 |
| 6. Organopolysiloxane of Synthesis Example 4 | 2.0 |
| 7. Aluminum distearate salt | 0.2 |
| 8. Magnesium sulfate | 0.7 |
| 9. Glycerin | 5.0 |
| 10. Preservative | appropriate amount |
| 11. Fragrance | appropriate amount |
| 12. Purified water | remainder |

(Preparation Method)

A: Components 1 to 7 were mixed with heating.

B: Components 8 to 10 and component 12 were dissolved by heating.

C: The solution obtained in B was gradually added into the mixture obtained in A with agitation for emulsification; and then, after cooling, component 11 was added into this emulsified mixture to obtain the milky lotion.

(Evaluation)

The milky lotion thus obtained was highly fine and low viscous while having wide and light spreading properties with a moist, vivid, and refreshing use feeling without stickiness and greasiness. In addition, it was excellent in temporal stability and cosmetic sustainability on a skin.

Example 17

Sunscreen Cream

| (Components) | (%) |
|---|---|
| 1. Decamethyl cyclopentasiloxane | 18.0 |
| 2. Methyl phenyl polysiloxane | 2.0 |
| 3. Liquid Paraffin | 1.5 |
| 4. Organopolysiloxane of Synthesis Example 3 | 4.0 |
| 5. Octyl p-methoxycinnamate | 5.0 |
| 6. 1,3-Butylene glycol | 4.0 |
| 7. Sodium chloride | 1.0 |
| 8. Preservative | appropriate amount |
| 9. Fragrance | appropriate amount |
| 10. Purified water | remainder |

(Preparation Method)

A: Components 1 to 5 were mixed with heating.

B: Components 6 to 8 and component 10 were dissolved by heating.

C: The solution obtained in B was gradually added into the mixture obtained in A with agitation for emulsification; and then, after cooling, component 9 was added into this emulsified mixture to obtain the sunscreen cream.

(Evaluation)

The sunscreen cream thus obtained was highly fine while having wide and light spreading properties with a moist and vivid use feeling, without stickiness and greasiness, and with good temporal stability. In addition, when the cream was applied to a skin, it showed excellent water-resistance and sweat-resistance with good cosmetic sustainability and durable UV-cut effect.

Example 18

Liquid Foundation

| (Components) | (%) |
|---|---|
| 1. Decamethyl cyclopentasiloxane | 16.0 |
| 2. Dimethyl polysiloxane (6 mm$^2$/second) | 8.0 |
| 3. Octyl p-methoxycinnamate | 3.0 |
| 4. 12-Hydroxystearic acid | 1.0 |
| 5. Fluorine-modified silicone (note 1) | 15.0 |
| 6. Organopolysiloxane of Synthesis Example 1 | 5.0 |
| 7. Spherical silicone resin powder (note 2) | 3.0 |
| 8. Titanium oxide microparticle treated with a fluorine-containing compound (note 3) | 8.0 |
| 9. Mica titanium treated with a fluorine-containing compound (note 3) | 1.0 |
| 10. Titanium oxide treated with a fluorine-containing compound (note 3) | 5.0 |
| 11. Red iron oxide treated with a fluorine-containing compound (note 3) | 0.9 |
| 12. Yellow iron oxide treated with a fluorine-containing compound (note 3) | 2.0 |
| 13. Black iron oxide treated with a fluorine-containing compound (note 3) | 1.0 |
| 14. Ethanol | 15.0 |
| 15. Glycerin | 3.0 |
| 16. Magnesium sulfate | 1.0 |
| 17. Preservative | appropriate amount |
| 18. Fragrance | appropriate amount |
| 19. Purified water | remainder |

(note 1)
(fluorine-modified silicone): FL-100 (manufactured by Shin-Etsu Chemical Co., Ltd.)
(note 2)
(spherical silicone resin powder): KMP 590 (manufactured by Shin-Etsu Chemical Co., Ltd.)
(note 3)
(treatment with a fluorine-containing compound): the powder is coated by 5% thereof with a diethanol amine perfluoroalkyl ethyl phosphate salt.

(Preparation Method)

A: Components 7 to 13 were mixed uniformly.

B: Components 1 to 6 were mixed by heating at 70° C., and then the mixture obtained in A was added thereinto; the resulting mixture was mixed and dispersed uniformly.

C: Components 14 to 17 and component 19 were heated to 40° C. to obtain a solution, which was then gradually added into the dispersed mixture obtained in B for emulsification; and then, after cooling, component 18 was added into this emulsified mixture to obtain the liquid foundation.

(Evaluation)

The liquid foundation thus obtained had wide and light spreading properties with a refreshing use feeling without stickiness. In addition, it showed no temporal change.

Example 19

Milky Lotion

| (Components) | (%) |
|---|---|
| 1. Decamethyl cyclopentasiloxane | 15.0 |
| 2. Methyl phenyl polysiloxane | 5.0 |
| 3. Squalene | 5.0 |
| 4. Pentaerythritol tetra-2-ethylhexanoate | 5.0 |
| 5. Organopolysiloxane of Synthesis Example 5 | 3.0 |
| 6. Organopolysiloxane elastomer spherical powder (note 1) | 2.0 |
| 7. Hydrophobized silica (note 2) | 0.5 |
| 8. Magnesium ascorbate phosphate | 1.0 |
| 9. Sodium chloride | 1.0 |
| 10. Polyethylene glycol 11000 | 1.0 |
| 11. Propylene glycol | 8.0 |
| 12. Preservative | appropriate amount |
| 13. Fragrance | appropriate amount |
| 14. Purified water | remainder |

(note 1)
(organopolysiloxane elastomer spherical powder): KMP 594 (manufactured by Shin-Etsu Chemical Co., Ltd.)
(note 2)
(hydrophobized silica): Aerosil R972 (manufactured by Nippon Aerosil Co. Ltd.)

(Preparation Method)

A: Components 1 to 5 were mixed uniformly, and then components 6 to 7 were added thereinto and the resulting mixture was dispersed uniformly.

B: Components 8 to 10 were added into component 14 for dissolution, and then a mixture of components 11 and 12 was added thereinto.

C: The mixture obtained in B was gradually added into the dispersed mixture obtained in A for emulsification; and then, after cooling, component 13 was added into this emulsified mixture to obtain the milky lotion.

(Evaluation)

The milky lotion thus obtained had wide and light spreading properties with a sleek use feeling without stickiness. In addition, it showed no temporal change.

Example 20

Moisturizing Cream

| (Components) | (%) |
|---|---|
| 1. Decamethyl cyclopentasiloxane | 10.0 |
| 2. Methyl phenyl polysiloxane | 3.0 |
| 3. Liquid paraffin | 5.0 |
| 4. Pentaerythritol tetra-2-ethylhexanoate | 3.0 |
| 5. Cetyl 2-ethylhexanoate | 5.0 |
| 6. Organopolysiloxane of Synthesis Example 1 | 1.0 |
| 7. Organopolysiloxane elastomer spherical powder (note 1) | 2.5 |
| 8. Hydrophobized silica (note 2) | 2.0 |
| 9. Zinc stearate | 2.0 |
| 10. Vitamin E acetate | 3.0 |
| 11. Polyethylene glycol 400 | 1.0 |
| 12. Sodium lactate | 1.0 |
| 13. 1,3-Butylene glycol | 5.0 |
| 14. Preservative | appropriate amount |
| 15. Fragrance | appropriate amount |
| 16. Purified water | remainder |

(note 1)
(organopolysiloxane elastomer spherical powder): KMP 594 (manufactured by Shin-Etsu Chemical Co., Ltd.)
(note 2)
(hydrophobized silica): Aerosil R972 (manufactured by Nippon Aerosil Co. Ltd.)

(Preparation Method)

A: Components 1 to 6 and components 9 to 10 were mixed uniformly, and then components 7 to 8 were added thereinto and the resulting mixture was dispersed uniformly.

B: Components 11 to 14 and component 16 were mixed for dissolution.

C: The solution obtained in B was gradually added into the mixture obtained in A for emulsification; and then, after cooling, component 15 was added into this emulsified mixture to obtain the moisturizing cream.

(Evaluation)

The moisturizing cream thus obtained had wide and light spreading properties without stickiness. In addition, it showed no temporal change.

Example 21

Eye Liner

| (Components) | (%) |
|---|---|
| 1. Decamethyl cyclopentasiloxane | 22.0 |
| 2. Dimethyl polysiloxane (6 mm$^2$/second) | 5.0 |
| 3. Silicone-treated black iron oxide | 20.0 |
| 4. Vitamin E acetate | 0.2 |
| 5. Jojoba oil | 2.0 |
| 6. Bentonite | 3.0 |
| 7. Organopolysiloxane of Synthesis Example 6 | 2.0 |
| 8. Ethanol | 10.0 |
| 9. 1,3-Butylene glycol | 10.0 |
| 10. Preservative | appropriate amount |
| 11. Fragrance | appropriate amount |
| 12. Purified water | remainder |

(Preparation Method)

A: Components 1 to 2 were mixed with components 4 to 7, and then component 3 was added thereinto and the resulting mixture was dispersed uniformly.

B: Components 8 to 10 were mixed with component 12.

C: The mixture obtained in B was gradually added into the dispersed mixture obtained in A for emulsification; and then, after cooling, component 11 was added into this emulsified mixture to obtain the eye liner.

(Evaluation)

The eye liner thus obtained had light spreading properties with easy drawing and without temporal change. In addition, it showed excellent water-resistance and sweat-resistance with good cosmetic sustainability on a skin.

Example 22

Sun-Cut Cream

| (Components) | (%) |
|---|---|
| 1. Decamethyl cyclopentasiloxane | 17.5 |
| 2. KP 545 (note 1) | 12.0 |
| 3. Glyceryl triisooctanoate | 5.0 |
| 4. Octyl p-methoxycinnamate | 6.0 |
| 5. KSG 210 (note 2) | 5.0 |
| 6. Organopolysiloxane of Synthesis Example 1 | 1.0 |
| 7. Lipophilized zinc oxide | 20.0 |
| 8. Sodium chloride | 0.5 |
| 9. 1,3-Butylene glycol | 2.0 |
| 10. Preservative | appropriate amount |
| 11. Fragrance | appropriate amount |
| 12. Purified water | remainder |

(note 1):
(KP 545): acryl silicone (manufactured by Shin-Etsu Chemical Co., Ltd.)
(note 2):
(KSG 210): silicone gel (manufactured by Shin-Etsu Chemical Co., Ltd.)

(Preparation Method)

A: Component 2 was mixed with a part of component 1 uniformly, and then component 7 was added thereinto: the resulting mixture was dispersed with a bead mill.

B: The rest of component 1 and component 3 to 6 were mixed uniformly.

C: Components 8 to 10 and component 12 were mixed and dissolved.

D: The solution obtained in C was added into the mixture obtained in B and they were emulsified; and then, A and component 11 were added into this emulsified mixture to obtain the sun-cut cream.

(Evaluation)

The sun-cut cream thus obtained had wide and light spreading properties with a good contact feeling without stickiness. In addition, it showed no temporal change with durable UV-cut effect on a skin.

Example 23

O/W Hand Cream

| (Components) | (%) |
|---|---|
| 1. KP 545 (note 1) | 10.0 |
| 2. KSG 16 (note 2) | 2.0 |
| 3. Isoparaffin | 5.0 |
| 4. Vaseline | 5.0 |
| 5. Glyceryl triisooctanoate | 3.0 |
| 6. Organopolysiloxane of Synthesis Example 4 | 0.5 |
| 7. Polyoxyethylene sorbitan monooleate | 1.0 |
| 8. Sepigel 305 (note 3) | 2.0 |
| 9. 1,3-Butylene glycol | 5.0 |
| 10. Glycerin | 5.0 |
| 11. Preservative | appropriate amount |
| 12. Fragrance | appropriate amount |
| 13. Purified water | remainder |

(note 1)
(KP 545): acryl silicone (manufactured by Shin-Etsu Chemical Co., Ltd.)
(note 2)
(KSG 16): silicone gel (manufactured by Shin-Etsu Chemical Co., Ltd.)
(note 3):
Sepigel 305 (manufactured by SEPPIC S. A.)

(Preparation Method)

A: Components 1 to 7 were mixed uniformly.

B: Components 8 to 11 and component 13 were mixed uniformly.

C: The solution obtained in B was added into the mixture obtained in A and they were emulsified; and then, component 12 was added into this emulsified mixture to obtain the O/W hand cream.

(Evaluation)

The O/W hand cream thus obtained had wide and light spreading properties with a good contact feeling and with effective protection of a skin during wet work. In addition, it showed no temporal change.

Example 24

O/W Hand Cream

| (Components) | (%) |
|---|---|
| 1. KP 545 (note 1) | 10.0 |
| 2. KS 561P (note 2) | 8.0 |

-continued

| (Components) | (%) |
|---|---|
| 3. Cetanol | 1.0 |
| 4. Glyceryl triisostearate | 5.0 |
| 5. Stearic acid | 3.0 |
| 6. Glyceryl monostearate | 1.5 |
| 7. Organopolysiloxane of Synthesis Example 2 | 0.7 |
| 8. Sorbitan sesquioleate | 0.5 |
| 9. Polyoxyethylene sorbitan monooleate | 1.0 |
| 10. Sodium hydroxide (1% aqueous solution) | 10.0 |
| 11. 1,3-Butylene glycol | 5.0 |
| 12. Preservative | appropriate amount |
| 13. Fragrance | appropriate amount |
| 14. Purified water | remainder |

(note 1)
(KP 545): acryl silicone (manufactured by Shin-Etsu Chemical Co., Ltd.)
(note 2)
(KP 561P): stearyl-modified acryl silicone (manufactured by Shin-Etsu Chemical Co., Ltd.)

(Preparation Method)

A: Components 1 to 9 were mixed and dissolved by heating.

B: Components 10 to 12 and component 14 were mixed with heating.

C: The mixture obtained in B was added into the solution obtained in A and they were emulsified; and then, after cooling, component 13 was added into this emulsified mixture to obtain the ON hand cream.

(Evaluation)

The O/W hand cream thus obtained had wide and light spreading properties with a good contact feeling, with effective protection of a skin during wet work, and without stickiness. In addition, it showed no temporal change.

As explained above, according to the present invention, it was shown that an organopolysiloxane having excellent emulsion stability, and in addition, excellent powder-dispersion stability if powders were contained therein, excellent temporal stability, and excellent skin-contact property could be provided; and in addition, a cosmetic containing this could be provided. Especially, if the organopolysiloxane mentioned above is blended in a powder-containing cosmetic, a cosmetic having highly dispersed powders may be obtained by powder-treatment effects (water resistance, cortical resistance, and dispersion stability into an oil material).

It must be noted here that the present invention is not limited to the embodiments shown above. The embodiments shown above are mere examples so that any embodiments composed of substantially the same technical concept as disclosed in the claims of the present invention and expressing a similar effect thereto are included in the technical scope of the present invention.

What is claimed is:

1. An organopolysiloxane shown by the following formula (1);

$$R^1-\underset{R^1}{\underset{|}{\overset{R^1}{\overset{|}{Si}}}}-\left(O-\underset{R^1}{\underset{|}{\overset{R^1}{\overset{|}{Si}}}}\right)_m-R^2-O-(C_3H_5(OR^3)O)_n-R^2-\left(\underset{R^1}{\underset{|}{\overset{R^1}{\overset{|}{Si}}}}-O\right)_m-\underset{R^1}{\underset{|}{\overset{R^1}{\overset{|}{Si}}}}-R^1,\tag{1}$$

wherein

"m" represents an integer of 2 to 100 and "n" represents an integer of 1 to 10;

each $R^1$ independently represents a group selected from
 an alkyl group having 1 to 30 carbon atoms,
 an aryl group having 6 to 30 carbon atoms, and
 an aralkyl group having 7 to 30 carbon atoms,
 wherein the alkyl group is optionally substituted with a fluorine atom;

each $R^2$ independently represents a divalent organic group having 2 to 15 carbon atoms and optionally intervened with an oxygen atom; and each $R^3$ independently represents a group selected from a polyoxyalkylene group shown by the following formula (2), and a group shown by the following formula (3);
wherein at least one of $R^3$ in one molecule is the polyoxyalkylene group shown by the formula (2), $$-(C_2H_4O)_a(C_3H_6O)_b(C_4H_8O)_c(C_5H_{10}O)_dR^4, \tag{2}$$

wherein $R^4$ represents a hydrogen atom, and each of "a", "b", "c", and "d" is independently an integer of 0 to 50 and $1 \leq (a+b+c+d) \leq 50$, $$-R^2-\left(\underset{R^1}{\underset{|}{\overset{R^1}{\overset{|}{Si}}}}-O\right)_m-\underset{R^1}{\underset{|}{\overset{R^1}{\overset{|}{Si}}}}-R^1, \tag{3}$$

wherein $R^1$ and $R^2$ represent the same meanings as before, and "m" represents an integer of 2 to 100.

2. The organopolysiloxane according to claim 1, wherein $R^2$ represents a divalent organic group shown by —$C_3H_6$— and $R^3$ represents a polyoxyalkylene group shown by the following formula (4);

$$-(C_2H_4O)_a(C_3H_6O)_bR^4, \tag{4}$$

wherein each of "a" and "b" is independently an integer of 0 to 50 and $1 \leq (a+b) \leq 50$, and $R^4$ represents the same meaning as in claim 1.

3. The organopolysiloxane according to claim 1, wherein $R^2$ represents a divalent organic group shown by —$C_3H_6$— and each $R^3$ independently represents a polyoxyalkylene group shown by the following formula (4) and the group shown by the formula (3), with "n" representing an integer of 2 to 10;

$$-(C_2H_4O)_a(C_3H_6O)_bR^4, \tag{4}$$

wherein each of "a" and "b" is independently an integer of 0 to 50 and $1 \leq (a+b) \leq 50$, and $R^4$ represents the same meaning as in claim 1.

4. A cosmetic wherein the organopolysiloxane according to claim 1 is contained therein with the amount thereof being 0.1 to 40% by mass relative to the total amount of the cosmetic.

5. The cosmetic according to claim 4, wherein the cosmetic further contains water and is in the form of an emulsion.

6. The cosmetic according to claim 4, wherein the cosmetic further contains any of a silicone oil, a glycol, an ester oil, a glyceride oil, and a mixture of them, and is in the form of a non-aqueous emulsion.

7. The cosmetic according to claim 4, wherein the cosmetic further contains a powder and is in the form of a liquid, a paste, or a solid, with the powder being dispersed therein.

* * * * *